(12) United States Patent
Berdel et al.

(10) Patent No.: US 7,618,943 B2
(45) Date of Patent: Nov. 17, 2009

(54) FUSION POLYPEPTIDES, AND USE THEREOF IN ANTIVASCULAR TUMOR THERAPY

(75) Inventors: Wolfgang E. Berdel, Münster (DE); Rolf M. Mesters, Münster (DE)

(73) Assignee: Oncoscience AG, Wedel (DE)

( * ) Notice: Subject to any disclaimer, the term of this patent is extended or adjusted under 35 U.S.C. 154(b) by 109 days.

(21) Appl. No.: 10/569,076

(22) PCT Filed: Aug. 20, 2004

(86) PCT No.: PCT/EP2004/009364

§ 371 (c)(1),
(2), (4) Date: Aug. 23, 2006

(87) PCT Pub. No.: WO2005/021593

PCT Pub. Date: Mar. 10, 2005

(65) Prior Publication Data

US 2007/0032419 A1    Feb. 8, 2007

(30) Foreign Application Priority Data

Aug. 22, 2003 (DE) .............................. 103 38 733

(51) Int. Cl.
| | |
|---|---|
| A61K 38/36 | (2006.01) |
| A61K 38/17 | (2006.01) |
| C12P 21/04 | (2006.01) |
| C12N 15/00 | (2006.01) |
| C12N 5/00 | (2006.01) |
| A61K 31/70 | (2006.01) |
| C07K 14/745 | (2006.01) |
| C07H 21/04 | (2006.01) |

(52) U.S. Cl. .......................... 514/12; 530/350; 530/381; 435/320.1; 435/325; 435/69.7; 536/23.4; 536/23.5; 514/44

(58) Field of Classification Search ........................ None
See application file for complete search history.

(56) References Cited

U.S. PATENT DOCUMENTS 7,425,328 B2 *   9/2008   Wang ....................... 424/143.1
2006/0088524 A1 *  4/2006   Morrissey et al. ......... 424/133.1

FOREIGN PATENT DOCUMENTS

WO    WO 03/035688 A    5/2003

OTHER PUBLICATIONS

Arap et al., "Cancer Treatment by Targeted Drug Delivery to Tumor Vasculature in a Mouse Model", Science 279:377-380 (1998).
Banner et al., "The Crystal Structure of the Complex of Blood Coagulation Factor VIIa with Soluble Tissue Factor", Nature 380:41-46 (1996).
Bhagwa et al., "CD13/APN is Activated by Angiogenic Signals and is Essential for Capillary Tube Formation", Blood 97(3):652-659 (2001).
Brooks et al., "Requirement of Vascular Integrin $\alpha_v\beta_3$ for Angiogenesis", Science 264:569-571 (1994).
Brooks et al., "Integrin $\alpha_v\beta_3$ Antagonists Promote Tumor Regression by Inducing Apoptosis of Angiogenic Blood Vessels", Cell 79:1157-1164 (1994).
Brooks et al., "Localization of Matrix Metalloproteinase MMP-2 to the Surface of Invasive Cells by Interaction with Integrin $\alpha_v\beta_3$", Cell 85:683-693 (1996).
Brooks et al., "Disruption of Angiogenesis by PEX, a Noncatalytic Metalloproteinase Fragment with Integrin Binding Activity", Cell, 92:391-400 (1998).
Burg et al., "NG2 Proteoglycan-Binding Peptides Target Tumor Neovasculature", Cancer Research 59:2869-2874 (1999).
Burrows et al., "Up-Regulation of Endoglin on Vascular Endothelial Cells in Human Solid Tumors: Implications for Diagnosis and Therapy", Clinical Cancer Research 1:1623-1634 (1995).
Carnemolla et al., "A Tumor-associated Fibronectin Isoform Generated by Alternative Splicing of Messenger RNA Precursors", The Journal of Cell Biology 108:1139-1148 (1989).
Curnis et al., "Enhancement of Tumor Necrosis Factor α Antitumor Immunotherapeutic Properties by Targeted Delivery to Aminopeptidase N (CD13)", Nature Biotechnology 18:1185-1190 (2000).
Curnis et al., "Differential Binding of Drugs Containing the NGR Motif to CD13 Isoforms in Tumor Vessels, Epithelia, and Myeloid Cells", Cancer Research 62:867-874 (2002).
Dvorak et al., "Distribution of Vascular Permeability Factor (Vascular Endothelial Growth Factor) in Tumors: Concentration in Tumor Blood Vessels", J. Exp Med. 174:1275-1278 (1991).
Dvorak et al., "Vascular Permeability Factor/Vascular Endothelial Growth Factor, Microvascular Hyperpermeability, and Angiogenesis", American Journal of Pathology, 146(5):1029-1039 (1995).
Ellerby et al., "Anti-Cancer Activity of Targeted Pro-Apoptotic Peptides", Nature Medicine, 5(9):1032-1038 (1999).
Folkman et al., "Induction of Angiogenesis During the Transition from Hyperplasia to Neoplasia", Nature 339:58-61 (1989).
Gottstein et al., "Generation and Characterization of Recombinant Vascular Targeting Agents from Hybridoma Cell Lines", BioTechniques 30(1):190-199 (2001).
Healy et al., "Peptide Ligands for Integrn $\alpha_v\beta_3$ Selected from Random Phage Display Libraries", Biochemistry 34:3948-3955 (1995).
Hu et al., "Comparison of Three Different Targeted Tissue Factor Fusion Proteins for Inducing Tumor Vessel Thrombosis", Cancer Research 63:5046-5053 (2003).
Huang et al., "Tumor Infarction in Mice by Antibody-directed Targeting of Tissue Factor to Tumor Vasculature", Science 275:547-550 (1997).
Koivunen et al., "Selection of Peptides Binding to the $\alpha_5\beta_1$ Integrin from Phage Display Library", The Journal of Biological Chemistry, 268(27):20205-20210 (1993).
Koivunen et al., "Tumor Targeting with a Selective Gelatinase Inhibitor", Nature Biotechnology 17:768-774 (1999).

(Continued)

Primary Examiner—Marianne P Allen
(74) Attorney, Agent, or Firm—Arnold & Porter LLP

(57) ABSTRACT

The present invention relates to fusion polypeptides, comprising at least two peptides. The invention further relates to the use of these fusion proteins in antivascular therapy of neoplastic diseases and to their use I the production of a drug for the treatment of neoplastic diseases.

24 Claims, 22 Drawing Sheets

OTHER PUBLICATIONS

Liu et al., "Prostate-specific Membrane Antigen Directed Selective Thrombotic Infarction of Tumors", *Cancer Research* 62:5470-5475 (2002).

Maisonpierre et al., "Angiopoietin-2, a Natural Antagonist for Tie2 That Disrupts In Vivo Angiogenesis", *Science* 277:55-60 (1997).

Morrissey et at, "Quantitation of Activated Factor VII Levels in Plasma Using a Tissue Factor Mutant Selectively Deficient in Promoting Factor VII Activation", *Blood* 81(3):734-744 (1993).

Nilsson et al., "Targeted Delivery of Tissue Factor to the ED-B Domain of Fibronectin, a Marker of Angiogenesis, Mediates the Infarction of Solid Tumors in Mice", *Cancer Research* 61:711-716 (2001).

Olsen et al., "Targeting the Tumor Vasculature: Inhibition of Tumor Growth by a Vascular Endothelial Growth Factor-Toxin Conjugate", *Int. J. Cancer* 73:865-870 (1997).

Pasqualini et al., "Aminopeptidase N Is a Receptor for Tumor-homing Peptides and a Target for Inhibiting Angiogenesis", *Cancer Research* 60:722-727 (2000).

Peters et al., "Expression of Tie2/Tek in Breast Tumour Vasculature Provides a New Marker for Evaluation of Tumour Angiogenesis", *British Journal of Cancer* 77(1):51-56 (1998).

Ran et al., "Infarction of Solid Hodgkin's Tumors in Mice by Antibody-directed Targeting of Tissue Factor to Tumor Vascularture", *Cancer Research* 58:4646-4653 (1998).

Rettig et al., "Identification of Endosialin, a Cell Surface Glycoprotein of Vascular Endothelial Cells in Human Cancer", *Proc. Natl. Acad. Sci. USA* 89:10832-10836 (1992).

Rippmann et al., "Fusion of the Tissue Factor Extracellular Domain to a Tumour Stromaspecific Single-Chain Fragment Variable Antibody Results in an Antigen-Specific Coagulation-Promoting Molecule", *Giochemical Journal* 349(3):805-812 (2000).

Ruf et al., "Phospholipid-independent and -dependent Interactions Required for Tissue Factor Receptor and Cofactor Function", *The Journal of Biological Chemistry*, 266(4):2158-2166 (1991).

Ruoslahti, "Targeting Tumor Vasculature with Homing Peptides from Phage Display", *Seminars in Cancer Biology* 10:435-442 (2000).

Scholz et al., "Correlation of Drug Response in Patients and in the Clonogenic Assay with Solid Human Tumour Xenografts", *Eur. J. Cancer* 26(8):901-905 (1990).

Schnürch et al., "Expression of tie-2, a Member of a Novel Family of Receptor Tyrosine Kinases, In the Endothelial Cell Lineage", *Development* 119:957-968 (1993).

Schrappe et al., "Correlation of Chondroitin Sulfate Proteoglycan Expression on Proliferating Brain Capillary Endothelial Cells with the Malignant Phenotype of Astroglial Cells", *Cancer Research* 51:4986-4993 (1991).

Senger et al., "Angiogenesis Promoted by Vascular Endothelial Growth Factor: Regulation Through $\alpha_1\beta_1$ and $\alpha_2\beta_1$ Integrins", *Proc. Natl. Acad. Sci. USA* 94:13612-13617 (1997).

Suri et al., "Requisite Role of Angiopoietin-1, a Ligand for the TIE2 Receptor, During Embryonic Angiogenesis", *Cell* 87:1171-1180 (1996).

Terman et al., "Biological Properties of VEGF/VPF Receptors", *Cancer and Metastasis Reviews* 15:159-163 (1996).

Topp et al., "Recombinant Human Interleukin-4 Inhibits Growth of Soe Human Lung Tumor Cell Lines In Vitro and In Vivo", *Blood* 82(9):2837-2844 (1993).

Topp et al., "Recombinant Human Interleukin 4 Has Antiproliferative Activity on Human Tumor Cell Lines Derived from Epithelial and Nonepithelial Histologies", *Cancer Research* 55:2173-2176 (1995).

Yun et al., "Involvement of Integrin $\alpha_v\beta_3$ in Cell Adhesion, Motility, and Liver Metastasis of Murine RAW117 Large Cell Lymphoma", *Cancer Research* 56:3103-3111 (1996).

Kessler et al. "Generation of Fusion Proteins for Selective Occlusion of Tumor Vessels," Current Drug Discovery Technologies, 5:1-8 (2008).

Bieker et al., "Infarction of tumor vessels by NGR-peptide directed targeting of tissue factor. Experimental results and first-in-man experience," pp. 1-40, available online on Jan. 28, 2009 at http://bloodjournal.hematologylibrary.org/cgi/content/abstract/blood-2008-04-150318v1?ck=nck.

\* cited by examiner

Fig. 12:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFREIFYIIGAVVFVVIILVIILAISLHKCRKAGVGQSW
KENSPLNVS

Fig. 13:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFR

Fig. 14:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFRGRGDSD

Fig. 15:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFRGNGRAHA

Fig. 16

GTTNTVAAYNLTWKSTNFKTILEWEPKPVNQVYTVQISTKS
DWKSKCFYTTDTECDLTDEIVKDVKQTYLARVFSYPAGNVE
TGSAGEPLYENSPEFTPYLETNLGQPTIQSFEQVGTKVNVT
EDERTLVRRNNTFLSLRDVFGKDLIYTLYYWKSSSSGKKTA
TNTNEFLIDVDKGENYCFSVQAVIPSRTVNRKSTDSPVECM
QEKGEFRGALNGRSHAG

Fig. 17:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFRGCNGRCG

Fig. 18:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFRGCNGRCVSGCAGRC

Fig. 19:

SGTTNTVAAYNLTWKSTNFKTILEWEPKPVNQVYTVQISTKS
GDWKSKCFYTTDTECDLTDEIVKDVKQTYLARVFSYPAGNVE
STGSAGEPLYENSPEFTPYLETNLGQPTIQSFEQVGTKVNVT
VEDERTLVRRNNTFLSLRDVFGKDLIYTLYYWKSSSSGKKTA
KTNTNEFLIDVDKGENYCFSVQAVIPSRTVNRKSTDSPVECM
GQEKGEFRGCVLNGRMEC

Fig. 20:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGA

Fig. 21:
TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GAAGAGGTGATTCTCCA

Fig. 22:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GTAACGGAAGAGCACATGCA

Fig. 23:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GTGCTTTAAATGGAAGATCTCACGCTGGT

Fig. 24:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GCTGCAACGGTAGATGTGGT

Fig. 25:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GTTGTAATGGAAGATGTGTTTCTGGATGTGCAGGACGATGT

Fig. 26:

TCAGGCACTACAAATACTGTGGCAGCATATAATTTAACTTGGAAATCAACTAATTTCAAGACAA
TTTTGGAGTGGGAACCCAAACCCGTCAATCAAGTCTACACTGTTCAAATAAGCACTAAGTCAGGAG
ATTGGAAAAGCAAATGCTTTTACACAACAGACACAGAGTGTGACCTCACCGACGAGATTGTGAAG
GATGTGAAGCAGACGTACTTGGCACGGGTCTTCTCCTACCCGGCAGGGAATGTGGAGAGCACCGGT
TCTGCTGGGGAGCCTCTGTATGAGAACTCCCCAGAGTTCACACCTTACCTGGAGACAAACCTCGGA
CAGCCAACAATTCAGAGTTTTGAACAGGTGGGAACAAAAGTGAATGTGACCGTAGAAGATGAACG
GACTTTAGTCAGAAGGAACAACACTTTCCTAAGCCTCCGGGATGTTTTTGGCAAGGACTTAATTTAT
ACACTTTATTATTGGAAATCTTCAAGTTCAGGAAAGAAAACAGCCAAAACAAACACTAATGAGTTT
TTGATTGATGTGGATAAAGGAGAAAACTACTGTTTCAGTGTTCAAGCAGTGATTCCCTCCCGAACA
GTTAACCGGAAGAGTACAGACAGCCCGGTAGAGTGTATGGGCCAGGAGAAAGGGGAATTCAGAG
GATGCGTCTTAAATGGTAGGATGGAATGC

Fig. 27:

A: 5'-CATGCCATGGGATCAGGCACTACAAATACTGTGGCAGCATATAAT-3'
B: 5'-CGGGATCCTATTATCTGAATTCCCCTTTCTCCTGGCCCAT-3'

Fig. 28:

A: 5'-CATGCCATGGGATCAGGCACTACAAATACTGTGGCAGCATATAAT-3'
B: 5'-CGGGATCCTATTATGGAGAATCACCTCTTCCTCTGAATTCCCC-3'

Fig. 29:

A: 5'-CATGCCATGGGATCAGGCACTACAAATACTGTGGCAGCATATAAT-3'
B: 5'-CGGGATCCTATTATGCATGTGCTCTTCCGTTACCTCTGAATTCCCC-3'

Fig. 30:

A: 5'-CATGCCATGGGATCAGGCACTACAAATACTGTGGCAGCATATAAT-3'
B: 5'-CGGGATCCTATTAACCACATCTACCGTTGCAGCCTCTGAATTCCCC-3'

Fig. 31:

A: 5'-CATGCCATGGGATCAGGCACTACAAATACTGTGGCAGCATATAAT-3'
B: 5'-CGGGATCCTATTAACATCGTCCTGCACATCCAGAAACACATCTTCCATTACAACC
   TCTGAATTCCCC-3'

Fig. 32:

A: 5'-CATGCCATGGGATCAGGCACTACAAATACTGTGGCAGCATATAAT-3'
B: 5'-CGGGATCCTATTA GCA TTC CAT CCT ACC ATT TAA GAC GCA TCC TCTGAATTCCCC-3

Fig. 33:

A: 5'-CATGCCATGGGATCAGGCACTACAAATACTGTGGCAGCATATAAT-3'
B: 5'-CGGGATCCTATTA ACCAGCGTGAGATCTTCCATTTAAAGCACCTCTGAATTCCCC-3'

Fig. 34
a
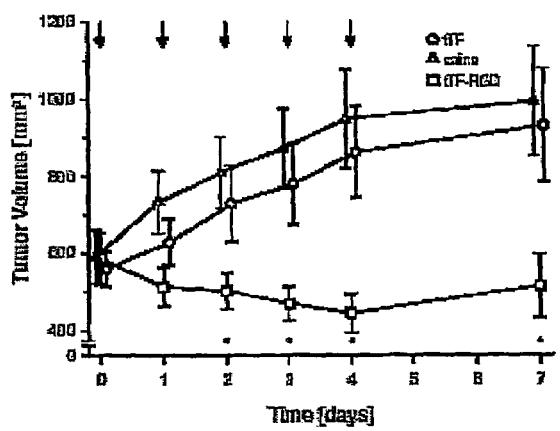
b
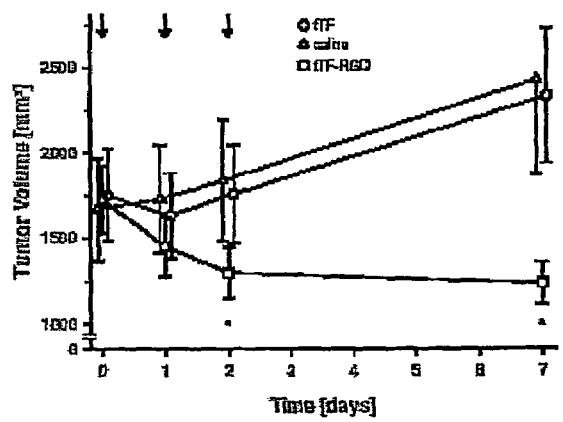
c
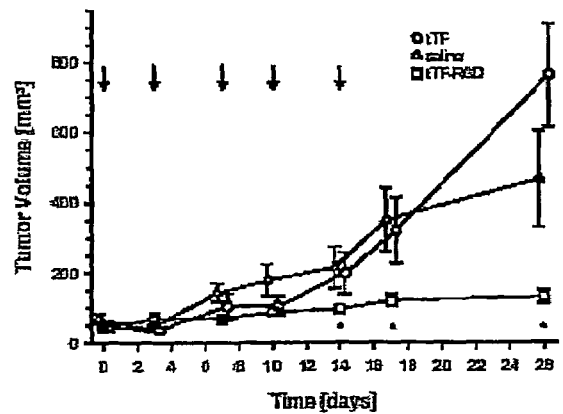

SEQUENCE LISTING

<160> NUMBER OF SEQ ID NOS: 41

<210> SEQ ID NO 1
<211> LENGTH: 263
<212> TYPE: PRT
<213> ORGANISM: Homo sapiens
<220> FEATURE:
<221> NAME/KEY: Amino acid sequence of human TF

<400> SEQUENCE: 1

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Ile Phe Tyr Ile Ile
    210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
            260
```

<210> SEQ ID NO 2
<211> LENGTH: 218
<212> TYPE: PRT
<213> ORGANISM: Homo sapiens
<220> FEATURE:
<221> NAME/KEY: Amino acid sequence of tTF1-218

<400> SEQUENCE: 2

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
```

```
                    20              25              30
Val Tyr Thr Val Gln Ile Ser Thr Lys Ser Gly Asp Trp Lys Ser Lys
        35                      40                      45

Cys Phe Tyr Thr Thr Asp Thr Glu Cys Asp Leu Thr Asp Glu Ile Val
    50                      55                      60

Lys Asp Val Lys Gln Thr Tyr Leu Ala Arg Val Phe Ser Tyr Pro Ala
65                      70                      75                  80

Gly Asn Val Glu Ser Thr Gly Ser Ala Gly Glu Pro Leu Tyr Glu Asn
                85                      90                      95

Ser Pro Glu Phe Thr Pro Tyr Leu Glu Thr Asn Leu Gly Gln Pro Thr
            100                     105                     110

Ile Gln Ser Phe Glu Gln Val Gly Thr Lys Val Asn Val Thr Val Glu
        115                     120                     125

Asp Glu Arg Thr Leu Val Arg Arg Asn Asn Thr Phe Leu Ser Leu Arg
    130                     135                     140

Asp Val Phe Gly Lys Asp Leu Ile Tyr Thr Leu Tyr Tyr Trp Lys Ser
145                     150                     155                 160

Ser Ser Ser Gly Lys Lys Thr Ala Lys Thr Asn Thr Asn Glu Phe Leu
                165                     170                     175

Ile Asp Val Asp Lys Gly Glu Asn Tyr Cys Phe Ser Val Gln Ala Val
            180                     185                     190

Ile Pro Ser Arg Thr Val Asn Arg Lys Ser Thr Asp Ser Pro Val Glu
        195                     200                     205

Cys Met Gly Gln Glu Lys Gly Glu Phe Arg
    210                     215
```

<210> SEQ ID NO 3
<211> LENGTH: 224
<212> TYPE: PRT
<213> ORGANISM: Artificial
<220> FEATURE:
<221> NAME/KEY: Amino acid sequence of tTF-GRGDSP
<223> OTHER INFORMATION: Synthetic construct

<400> SEQUENCE: 3

```
Ser Gly Thr Thr Asn Thr Val Ala Ala Tyr Asn Leu Thr Trp Lys Ser
1               5                       10                      15

Thr Asn Phe Lys Thr Ile Leu Glu Trp Glu Pro Lys Pro Val Asn Gln
            20                      25                      30

Val Tyr Thr Val Gln Ile Ser Thr Lys Ser Gly Asp Trp Lys Ser Lys
        35                      40                      45

Cys Phe Tyr Thr Thr Asp Thr Glu Cys Asp Leu Thr Asp Glu Ile Val
    50                      55                      60

Lys Asp Val Lys Gln Thr Tyr Leu Ala Arg Val Phe Ser Tyr Pro Ala
65                      70                      75                  80

Gly Asn Val Glu Ser Thr Gly Ser Ala Gly Glu Pro Leu Tyr Glu Asn
                85                      90                      95

Ser Pro Glu Phe Thr Pro Tyr Leu Glu Thr Asn Leu Gly Gln Pro Thr
            100                     105                     110

Ile Gln Ser Phe Glu Gln Val Gly Thr Lys Val Asn Val Thr Val Glu
        115                     120                     125

Asp Glu Arg Thr Leu Val Arg Arg Asn Asn Thr Phe Leu Ser Leu Arg
    130                     135                     140

Asp Val Phe Gly Lys Asp Leu Ile Tyr Thr Leu Tyr Tyr Trp Lys Ser
145                     150                     155                 160
```

```
Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
                195                 200                 205

Cys Met Gly Gln Glu Lys Gly Glu Phe Arg Gly Arg Gly Asp Ser Asp
    210                 215                 220
```

<210> SEQ ID NO 4
<211> LENGTH: 225
<212> TYPE: PRT
<213> ORGANISM: Artificial
<220> FEATURE:
<221> NAME/KEY: Amino acid sequence of tTF-GNGRAHA
<223> OTHER INFORMATION: Synthetic construct

<400> SEQUENCE: 4

```
Ser Gly Thr Thr Asn Thr Val Ala Ala Tyr Asn Leu Thr Trp Lys Ser
1                   5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
                35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
                130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
                195                 200                 205

Cys Met Gly Gln Glu Lys Gly Glu Phe Arg Gly Asn Gly Arg Ala His
    210                 215                 220
Ala
225
```

<210> SEQ ID NO 5
<211> LENGTH: 228
<212> TYPE: PRT
<213> ORGANISM: Artificial
<220> FEATURE:
<221> NAME/KEY: Amino acid sequence of tTF-GALNGRSHAG
<223> OTHER INFORMATION: Synthetic construct

<400> SEQUENCE: 5

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
        50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
            130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Gly Ala Leu Asn Gly Arg
210                 215                 220

Ser His Ala Gly
225

<210> SEQ ID NO 6
<211> LENGTH: 225
<212> TYPE: PRT
<213> ORGANISM: Artificial
<220> FEATURE:
<221> NAME/KEY: Amino acid sequence of tTF-GCNGRCG
<223> OTHER INFORMATION: Synthetic construct

<400> SEQUENCE: 6

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
        50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125
```

```
Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
        180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Gly Cys Asn Gly Arg Cys
        210                 215                 220

Gly
225

<210> SEQ ID NO 7
<211> LENGTH: 232
<212> TYPE: PRT
<213> ORGANISM: Artificial
<220> FEATURE:
<221> NAME/KEY: Amino acid sequence of tTF-GCNGRCVSGCAGRC
<223> OTHER INFORMATION: Synthetic construct

<400> SEQUENCE: 7

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
        180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Gly Cys Asn Gly Arg Cys
        210                 215                 220

Val Ser Gly Cys Ala Gly Arg Cys
225                 230
```

```
<210> SEQ ID NO 8
<211> LENGTH: 228
<212> TYPE: PRT
<213> ORGANISM: Artificial
<220> FEATURE:
<221> NAME/KEY: Amino acid sequence of tTF-GCVLNGRMEC
<223> OTHER INFORMATION: Synthetic construct

<400> SEQUENCE: 8

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Gly Cys Val Leu Asn Gly
    210                 215                 220

Arg Met Glu Cys
225

<210> SEQ ID NO 9
<211> LENGTH: 654
<212> TYPE: DNA
<213> ORGANISM: Artificial Sequence
<220> FEATURE:
<221> NAME/KEY: Nucleotide sequence of tTF1-218
<223> OTHER INFORMATION: Synthetic construct

<400> SEQUENCE: 9
tcaggcacta caaatactgt ggcagcatat aatttaactt ggaaatcaac taatttcaag      60 acaatttttgg agtgggaacc caaacccgtc aatcaagtct acactgttca ataagcact    120 aagtcaggag attggaaaag caaatgcttt tacacaacag acacagagtg tgacctcacc    180
gacgagattg tgaaggatgt gaagcagacg tacttggcac gggtcttctc ctacccggca    240
gggaatgtgg agagcaccgg ttctgctggg gagcctctgt atgagaactc cccagagttc    300
acaccttacc tggagacaaa cctcggacag ccaacaattc agagttttga acaggtggga    360
acaaaagtga atgtgaccgt agaagatgaa cggactttag tcagaaggaa caacactttc    420
```

```
ctaagcctcc gggatgtttt tggcaaggac ttaatttata cactttatta ttggaaatct    480
tcaagttcag gaaagaaaac agccaaaaca aacactaatg agtttttgat tgatgtggat    540
aaaggagaaa actactgttt cagtgttcaa gcagtgattc cctcccgaac agttaaccgg    600
aagagtacag acagcccggt agagtgtatg ggccaggaga aggggaatt caga           654
```

<210> SEQ ID NO 10
<211> LENGTH: 672
<212> TYPE: DNA
<213> ORGANISM: Artificial
<220> FEATURE:
<221> NAME/KEY: Nucleotide sequence of tTF-GRGDSP
<223> OTHER INFORMATION: Synthetic construct

<400> SEQUENCE: 10

```
tcaggcacta caaatactgt ggcagcatat aatttaactt ggaaatcaac taatttcaag     60
acaattttgg agtgggaacc caaacccgtc aatcaagtct acactgttca aataagcact    120
aagtcaggag attggaaaag caaatgcttt tacacaacag acacagagtg tgacctcacc    180
gacgagattg tgaaggatgt gaagcagacg tacttggcac gggtcttctc ctacccggca    240
gggaatgtgg agagcaccgg ttctgctggg gagcctctgt atgagaactc cccagagttc    300
acaccttacc tggagacaaa cctcggacag ccaacaattc agagttttga acaggtggga    360
acaaaagtga atgtgaccgt agaagatgaa cggactttag tcagaaggaa caacactttc    420
ctaagcctcc gggatgtttt tggcaaggac ttaatttata cactttatta ttggaaatct    480
tcaagttcag gaaagaaaac agccaaaaca aacactaatg agtttttgat tgatgtggat    540
aaaggagaaa actactgttt cagtgttcaa gcagtgattc cctcccgaac agttaaccgg    600
aagagtacag acagcccggt agagtgtatg ggccaggaga aggggaatt cagaggaaga    660 ggtgattctc ca                                                        672
```

<210> SEQ ID NO 11
<211> LENGTH: 675
<212> TYPE: DNA
<213> ORGANISM: Artificial
<220> FEATURE:
<221> NAME/KEY: Nucleotide sequence of tTF-GNGRAHA
<223> OTHER INFORMATION: Synthetic construct

<400> SEQUENCE: 11

```
tcaggcacta caaatactgt ggcagcatat aatttaactt ggaaatcaac taatttcaag     60
acaattttgg agtgggaacc caaacccgtc aatcaagtct acactgttca aataagcact    120
aagtcaggag attggaaaag caaatgcttt tacacaacag acacagagtg tgacctcacc    180
gacgagattg tgaaggatgt gaagcagacg tacttggcac gggtcttctc ctacccggca    240
gggaatgtgg agagcaccgg ttctgctggg gagcctctgt atgagaactc cccagagttc    300
acaccttacc tggagacaaa cctcggacag ccaacaattc agagttttga acaggtggga    360
acaaaagtga atgtgaccgt agaagatgaa cggactttag tcagaaggaa caacactttc    420
ctaagcctcc gggatgtttt tggcaaggac ttaatttata cactttatta ttggaaatct    480
tcaagttcag gaaagaaaac agccaaaaca aacactaatg agtttttgat tgatgtggat    540
aaaggagaaa actactgttt cagtgttcaa gcagtgattc cctcccgaac agttaaccgg    600
aagagtacag acagcccggt agagtgtatg ggccaggaga aggggaatt cagaggtaac    660 ggaagagcac atgca                                                     675
```

<210> SEQ ID NO 12
<211> LENGTH: 684
<212> TYPE: DNA
<213> ORGANISM: Artificial
<220> FEATURE:
<221> NAME/KEY: Nucleotide sequence of tTF-GALNGRSHAG
<223> OTHER INFORMATION: Synthetic construct

<400> SEQUENCE: 12

```
tcaggcacta caaatactgt ggcagcatat aatttaactt ggaaatcaac taatttcaag      60
acaattttgg agtgggaacc caaacccgtc aatcaagtct acactgttca aataagcact     120
aagtcaggag attggaaaag caaatgcttt tacacaacag acacagagtg tgacctcacc     180
gacgagattg tgaaggatgt gaagcagacg tacttggcac gggtcttctc ctacccggca     240
gggaatgtgg agagcaccgg ttctgctggg agcctctgt atgagaactc cccagagttc     300
acaccttacc tggagacaaa cctcggacag ccaacaattc agagttttga acaggtggga     360
acaaaagtga atgtgaccgt agaagatgaa cggactttag tcagaaggaa caacactttc     420
ctaagcctcc gggatgtttt tggcaaggac ttaatttata cactttatta ttggaaatct     480
tcaagttcag gaaagaaaac agccaaaaca aacactaatg agttttgat tgatgtggat     540
aaaggagaaa actactgttt cagtgttcaa gcagtgattc cctcccgaac agttaaccgg     600
aagagtacag acagcccggt agagtgtatg ggccaggaga aggggaatt cagaggtgct     660
ttaaatggaa gatctcacgc tggt                                          684
```

<210> SEQ ID NO 13
<211> LENGTH: 675
<212> TYPE: DNA
<213> ORGANISM: Artificial
<220> FEATURE:
<221> NAME/KEY: Nucleotide sequence of tTF-GCNGRCG
<223> OTHER INFORMATION: Synthetic construct

<400> SEQUENCE: 13

```
tcaggcacta caaatactgt ggcagcatat aatttaactt ggaaatcaac taatttcaag      60
acaattttgg agtgggaacc caaacccgtc aatcaagtct acactgttca aataagcact     120
aagtcaggag attggaaaag caaatgcttt tacacaacag acacagagtg tgacctcacc     180
gacgagattg tgaaggatgt gaagcagacg tacttggcac gggtcttctc ctacccggca     240
gggaatgtgg agagcaccgg ttctgctggg agcctctgt atgagaactc cccagagttc     300
acaccttacc tggagacaaa cctcggacag ccaacaattc agagttttga acaggtggga     360
acaaaagtga atgtgaccgt agaagatgaa cggactttag tcagaaggaa caacactttc     420
ctaagcctcc gggatgtttt tggcaaggac ttaatttata cactttatta ttggaaatct     480
tcaagttcag gaaagaaaac agccaaaaca aacactaatg agttttgat tgatgtggat     540
aaaggagaaa actactgttt cagtgttcaa gcagtgattc cctcccgaac agttaaccgg     600
aagagtacag acagcccggt agagtgtatg ggccaggaga aggggaatt cagaggctgc     660
aacggtagat gtggt                                                    675
```

<210> SEQ ID NO 14
<211> LENGTH: 696
<212> TYPE: DNA
<213> ORGANISM: Artificial
<220> FEATURE:
<221> NAME/KEY: Nucleotide sequence of tTF-GCNGRCVSGCAGRC
<223> OTHER INFORMATION: Synthetic construct -continued

```
<400> SEQUENCE: 14
tcaggcacta caaatactgt ggcagcatat aatttaactt ggaaatcaac taatttcaag      60
acaattttgg agtgggaacc caaacccgtc aatcaagtct acactgttca ataagcact      120 aagtcaggag attggaaaag caaatgcttt tacacaacag acacagagtg tgacctcacc     180
gacgagattg tgaaggatgt gaagcagacg tacttggcac gggtcttctc ctacccggca     240
gggaatgtgg agagcaccgg ttctgctggg gagcctctgt atgagaactc cccagagttc     300
acaccttacc tggagacaaa cctcggacag ccaacaattc agagttttga acaggtggga     360
acaaaagtga atgtgaccgt agaagatgaa cggactttag tcagaaggaa caacactttc     420
ctaagcctcc gggatgtttt tggcaaggac ttaatttata cactttatta ttggaaatct     480
tcaagttcag gaaagaaaac agccaaaaca aacactaatg agttttgat tgatgtggat      540 aaaggagaaa actactgttt cagtgttcaa gcagtgattc cctcccgaac agttaaccgg     600
aagagtacag acagcccggt agagtgtatg ggccaggaga aaggggaatt cagaggttgt     660
aatggaagat gtgtttctgg atgtgcagga cgatgt                               696

<210> SEQ ID NO 15
<211> LENGTH: 684
<212> TYPE: DNA
<213> ORGANISM: Artificial
<220> FEATURE:
<221> NAME/KEY: Nucleotide sequence of tTF-GCVLNGRMEC
<223> OTHER INFORMATION: Synthetic construct

<400> SEQUENCE: 15
tcaggcacta caaatactgt ggcagcatat aatttaactt ggaaatcaac taatttcaag      60
acaattttgg agtgggaacc caaacccgtc aatcaagtct acactgttca ataagcact      120 aagtcaggag attggaaaag caaatgcttt tacacaacag acacagagtg tgacctcacc     180
gacgagattg tgaaggatgt gaagcagacg tacttggcac gggtcttctc ctacccggca     240
gggaatgtgg agagcaccgg ttctgctggg gagcctctgt atgagaactc cccagagttc     300
acaccttacc tggagacaaa cctcggacag ccaacaattc agagttttga acaggtggga     360
acaaaagtga atgtgaccgt agaagatgaa cggactttag tcagaaggaa caacactttc     420
ctaagcctcc gggatgtttt tggcaaggac ttaatttata cactttatta ttggaaatct     480
tcaagttcag gaaagaaaac agccaaaaca aacactaatg agttttgat tgatgtggat      540 aaaggagaaa actactgttt cagtgttcaa gcagtgattc cctcccgaac agttaaccgg     600
aagagtacag acagcccggt agagtgtatg ggccaggaga aaggggaatt cagaggatgc     660
gtcttaaatg gtaggatgga atgc                                            684

<210> SEQ ID NO 16
<211> LENGTH: 45
<212> TYPE: DNA
<213> ORGANISM: Artificial Sequence
<220> FEATURE:
<221> NAME/KEY: 5' Oligonucleotide primer for the preparation of
      tTF1-218
<223> OTHER INFORMATION: Synthetic construct

<400> SEQUENCE: 16
catgccatgg gatcaggcac tacaaatact gtggcagcat ataat                      45

<210> SEQ ID NO 17
<211> LENGTH: 40
<212> TYPE: DNA
```

```
<213> ORGANISM: Artificial Sequence
<220> FEATURE:
<221> NAME/KEY: 3' Oligonucleotide primer for the preparation of
      tTF1-218
<223> OTHER INFORMATION: Synthetic construct

<400> SEQUENCE: 17
cgggatccta ttatctgaat tcccctttct cctggcccat                40

<210> SEQ ID NO 18
<211> LENGTH: 45
<212> TYPE: DNA
<213> ORGANISM: Artificial
<220> FEATURE:
<221> NAME/KEY: 5' Oligonucleotide primer for the preparation of
      tTF-GRGDSP
<223> OTHER INFORMATION: Synthetic construct

<400> SEQUENCE: 18
catgccatgg gatcaggcac tacaaatact gtggcagcat ataat          45

<210> SEQ ID NO 19
<211> LENGTH: 43
<212> TYPE: DNA
<213> ORGANISM: Artificial
<220> FEATURE:
<221> NAME/KEY: 3' Oligonucleotide primer for the preparation of
      tTF-GRGDSP
<223> OTHER INFORMATION: Synthetic construct

<400> SEQUENCE: 19
cgggatccta ttatggagaa tcacctcttc ctctgaattc ccc            43

<210> SEQ ID NO 20
<211> LENGTH: 45
<212> TYPE: DNA
<213> ORGANISM: Artificial
<220> FEATURE:
<221> NAME/KEY: 5' Oligonucleotide primer for the preparation of
      tTF-GNGRAHA
<223> OTHER INFORMATION: Synthetic construct

<400> SEQUENCE: 20
catgccatgg gatcaggcac tacaaatact gtggcagcat ataat          45

<210> SEQ ID NO 21
<211> LENGTH: 46
<212> TYPE: DNA
<213> ORGANISM: Artificial
<220> FEATURE:
<221> NAME/KEY: 3' Oligonucleotide primer for the preparation of
      tTF-GNGRAHA
<223> OTHER INFORMATION: Synthetic construct

<400> SEQUENCE: 21
cgggatccta ttatgcatgt gctcttccgt tacctctgaa ttcccc         46

<210> SEQ ID NO 22
<211> LENGTH: 45
<212> TYPE: DNA
<213> ORGANISM: Artificial
<220> FEATURE:
<221> NAME/KEY: 5' Oligonucleotide primer for the preparation of
      tTF-GCNGRCG
<223> OTHER INFORMATION: Synthetic construct

<400> SEQUENCE: 22
catgccatgg gatcaggcac tacaaatact gtggcagcat ataat          45
```

<210> SEQ ID NO 23
<211> LENGTH: 46
<212> TYPE: DNA
<213> ORGANISM: Artificial
<220> FEATURE:
<221> NAME/KEY: 3' Oligonucleotide primer for the preparation of tTF-GCNGRCG
<223> OTHER INFORMATION: Synthetic construct

<400> SEQUENCE: 23
cgggatccta ttaaccacat ctaccgttgc agcctctgaa ttcccc    46

<210> SEQ ID NO 24
<211> LENGTH: 45
<212> TYPE: DNA
<213> ORGANISM: Artificial
<220> FEATURE:
<221> NAME/KEY: 5' Oligonucleotide primer for the preparation of tTF-GCNGRCVSGCAGRC
<223> OTHER INFORMATION: Synthetic construct

<400> SEQUENCE: 24
catgccatgg gatcaggcac tacaaatact gtggcagcat ataat    45

<210> SEQ ID NO 25
<211> LENGTH: 67
<212> TYPE: DNA
<213> ORGANISM: Artificial
<220> FEATURE:
<221> NAME/KEY: 3' Oligonucleotide primer for the preparation of tTF-GCNGRCVSGCAGRC
<223> OTHER INFORMATION: Synthetic construct

<400> SEQUENCE: 25
cgggatccta ttaacatcgt cctgcacatc cagaaacaca tcttccatta caacctctga    60
attcccc    67

<210> SEQ ID NO 26
<211> LENGTH: 45
<212> TYPE: DNA
<213> ORGANISM: Artificial
<220> FEATURE:
<221> NAME/KEY: 5' Oligonucleotide primer for the preparation of tTF-GCVLNGRMEC
<223> OTHER INFORMATION: Synthetic construct

<400> SEQUENCE: 26
catgccatgg gatcaggcac tacaaatact gtggcagcat ataat    45

<210> SEQ ID NO 27
<211> LENGTH: 55
<212> TYPE: DNA
<213> ORGANISM: Artificial
<220> FEATURE:
<221> NAME/KEY: 3' Oligonucleotide primer for the preparation of tTF-GCVLNGRMEC
<223> OTHER INFORMATION: Synthetic construct

<400> SEQUENCE: 27
cgggatccta ttagcattcc atcctaccat ttaagacgca tcctctgaat tcccc    55

<210> SEQ ID NO 28
<211> LENGTH: 45
<212> TYPE: DNA
<213> ORGANISM: Artificial
<220> FEATURE:

<221> NAME/KEY: 5' Oligonucleotide primer for the preparation of
      tTF-GALNGRSHAG
<223> OTHER INFORMATION: Synthetic construct

<400> SEQUENCE: 28
catgccatgg gatcaggcac tacaaatact gtggcagcat ataat         45

<210> SEQ ID NO 29
<211> LENGTH: 55
<212> TYPE: DNA
<213> ORGANISM: Artificial
<220> FEATURE:
<221> NAME/KEY: 3' Oligonucleotide primer for the preparation of
      tTF-GALNGRSHAG
<223> OTHER INFORMATION: Synthetic construct

<400> SEQUENCE: 29
cgggatccta ttaaccagcg tgagatcttc catttaaagc acctctgaat ccccc    55

<210> SEQ ID NO 30
<211> LENGTH: 45
<212> TYPE: PRT
<213> ORGANISM: Artificial
<220> FEATURE:
<221> NAME/KEY: Amino acid sequence of the affinity-tag
<223> OTHER INFORMATION: Synthetic construct

<400> SEQUENCE: 30

His His His His His His Ser Ser Gly Leu Val Pro Arg Gly Ser Gly
1               5                   10                  15

Met Lys Glu Thr Ala Ala Ala Lys Phe Glu Arg Gln His Met Asp Ser
            20                  25                  30

Pro Asp Leu Gly Thr Asp Asp Asp Lys Ala Met Gly
        35                  40                  45

<210> SEQ ID NO 31
<211> LENGTH: 269
<212> TYPE: PRT
<213> ORGANISM: Artificial
<220> FEATURE:
<221> NAME/KEY: Amino acid squence of tTF-GRGDSP having an N-terminal
      affinity-tag
<223> OTHER INFORMATION: Synthetic construct

<400> SEQUENCE: 31

His His His His His His Ser Ser Gly Leu Val Pro Arg Gly Ser Gly
1               5                   10                  15

Met Lys Glu Thr Ala Ala Ala Lys Phe Glu Arg Gln His Met Asp Ser
            20                  25                  30

Pro Asp Leu Gly Thr Asp Asp Asp Lys Ala Met Gly Ser Gly Thr
        35                  40                  45

Thr Asn Thr Val Ala Ala Tyr Asn Leu Thr Trp Lys Ser Thr Asn Phe
    50                  55                  60

Lys Thr Ile Leu Glu Trp Glu Pro Lys Pro Val Asn Gln Val Tyr Thr
65                  70                  75                  80

Val Gln Ile Ser Thr Lys Ser Gly Asp Trp Lys Ser Lys Cys Phe Tyr
                85                  90                  95

Thr Thr Asp Thr Glu Cys Asp Leu Thr Asp Glu Ile Val Lys Asp Val
                100                 105                 110

Lys Gln Thr Tyr Leu Ala Arg Val Phe Ser Tyr Pro Ala Gly Asn Val
            115                 120                 125

Glu Ser Thr Gly Ser Ala Gly Glu Pro Leu Tyr Glu Asn Ser Pro Glu

-continued

```
            130                 135                 140
Phe Thr Pro Tyr Leu Glu Thr Asn Leu Gly Gln Pro Thr Ile Gln Ser
145                 150                 155                 160

Phe Glu Gln Val Gly Thr Lys Val Asn Val Thr Val Glu Asp Glu Arg
                165                 170                 175

Thr Leu Val Arg Arg Asn Asn Thr Phe Leu Ser Leu Arg Asp Val Phe
            180                 185                 190

Gly Lys Asp Leu Ile Tyr Thr Leu Tyr Tyr Trp Lys Ser Ser Ser Ser
                195                 200                 205

Gly Lys Lys Thr Ala Lys Thr Asn Thr Asn Glu Phe Leu Ile Asp Val
210                 215                 220

Asp Lys Gly Glu Asn Tyr Cys Phe Ser Val Gln Ala Val Ile Pro Ser
225                 230                 235                 240

Arg Thr Val Asn Arg Lys Ser Thr Asp Ser Pro Val Glu Cys Met Gly
            245                 250                 255

Gln Glu Lys Gly Glu Phe Arg Gly Arg Gly Asp Ser Asp
                260                 265
```

<210> SEQ ID NO 32
<211> LENGTH: 270
<212> TYPE: PRT
<213> ORGANISM: Artificial
<220> FEATURE:
<221> NAME/KEY: Amino acid sequence of tTF-GNGRAHA having an N-terminal affinity-tag
<223> OTHER INFORMATION: Synthetic construct

<400> SEQUENCE: 32

```
His His His His His Ser Ser Gly Leu Val Pro Arg Gly Ser Gly
1               5                   10                  15

Met Lys Glu Thr Ala Ala Ala Lys Phe Glu Arg Gln His Met Asp Ser
                20                  25                  30

Pro Asp Leu Gly Thr Asp Asp Asp Lys Ala Met Gly Ser Gly Thr
            35                  40                  45

Thr Asn Thr Val Ala Ala Tyr Asn Leu Thr Trp Lys Ser Thr Asn Phe
50                  55                  60

Lys Thr Ile Leu Glu Trp Glu Pro Lys Pro Val Asn Gln Val Tyr Thr
65                  70                  75                  80

Val Gln Ile Ser Thr Lys Ser Gly Asp Trp Lys Ser Lys Cys Phe Tyr
                85                  90                  95

Thr Thr Asp Thr Glu Cys Asp Leu Thr Asp Glu Ile Val Lys Asp Val
            100                 105                 110

Lys Gln Thr Tyr Leu Ala Arg Val Phe Ser Tyr Pro Ala Gly Asn Val
                115                 120                 125

Glu Ser Thr Gly Ser Ala Gly Glu Pro Leu Tyr Glu Asn Ser Pro Glu
130                 135                 140

Phe Thr Pro Tyr Leu Glu Thr Asn Leu Gly Gln Pro Thr Ile Gln Ser
145                 150                 155                 160

Phe Glu Gln Val Gly Thr Lys Val Asn Val Thr Val Glu Asp Glu Arg
                165                 170                 175

Thr Leu Val Arg Arg Asn Asn Thr Phe Leu Ser Leu Arg Asp Val Phe
            180                 185                 190

Gly Lys Asp Leu Ile Tyr Thr Leu Tyr Tyr Trp Lys Ser Ser Ser Ser
                195                 200                 205

Gly Lys Lys Thr Ala Lys Thr Asn Thr Asn Glu Phe Leu Ile Asp Val
210                 215                 220
```

```
Asp Lys Gly Glu Asn Tyr Cys Phe Ser Val Gln Ala Val Ile Pro Ser
225                 230                 235                 240

Arg Thr Val Asn Arg Lys Ser Thr Asp Ser Pro Val Glu Cys Met Gly
                245                 250                 255

Gln Glu Lys Gly Glu Phe Arg Gly Asn Gly Arg Ala His Ala
            260                 265                 270

<210> SEQ ID NO 33
<211> LENGTH: 6
<212> TYPE: PRT
<213> ORGANISM: Artificial
<220> FEATURE:
<223> OTHER INFORMATION: Synthetic construct

<400> SEQUENCE: 33

Gly Arg Gly Asp Ser Pro
1               5

<210> SEQ ID NO 34
<211> LENGTH: 7
<212> TYPE: PRT
<213> ORGANISM: Artificial
<220> FEATURE:
<223> OTHER INFORMATION: Synthetic construct

<400> SEQUENCE: 34

Gly Asn Gly Arg Ala His Ala
1               5

<210> SEQ ID NO 35
<211> LENGTH: 10
<212> TYPE: PRT
<213> ORGANISM: Artificial
<220> FEATURE:
<223> OTHER INFORMATION: Synthetic construct

<400> SEQUENCE: 35

Gly Ala Leu Asn Gly Arg Ser His Ala Gly
1               5                   10

<210> SEQ ID NO 36
<211> LENGTH: 7
<212> TYPE: PRT
<213> ORGANISM: Artificial
<220> FEATURE:
<221> NAME/KEY: Cyclic
<223> OTHER INFORMATION: Synthetic construct

<400> SEQUENCE: 36

Gly Cys Asn Gly Arg Cys Gly
1               5

<210> SEQ ID NO 37
<211> LENGTH: 14
<212> TYPE: PRT
<213> ORGANISM: Artificial
<220> FEATURE:
<221> NAME/KEY: Cyclic
<223> OTHER INFORMATION: Synthetic construct

<400> SEQUENCE: 37

Gly Cys Asn Gly Arg Cys Val Ser Gly Cys Ala Gly Arg Cys
1               5                   10

<210> SEQ ID NO 38
```

```
<211> LENGTH: 10
<212> TYPE: PRT
<213> ORGANISM: Artificial
<220> FEATURE:
<221> NAME/KEY: Cyclic
<223> OTHER INFORMATION: Synthetic construct

<400> SEQUENCE: 38

Gly Cys Val Leu Asn Gly Arg Met Glu Cys
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic Construct

<400> SEQUENCE: 39

Thr Ala Ala Ser Gly Val Arg Ser Met His
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic Construct

<400> SEQUENCE: 40

Leu Thr Leu Arg Trp Val Gly Leu Met Ser
1               5                   10

<210> SEQ ID NO 41
<211> LENGTH: 8
<212> TYPE: PRT
<213> ORGANISM: Artificial
<220> FEATURE:
<223> OTHER INFORMATION: Synthetic construct

<400> SEQUENCE: 41

Thr Thr His Trp Gly Phe Thr Leu
1               5
```

FUSION POLYPEPTIDES, AND USE THEREOF IN ANTIVASCULAR TUMOR THERAPY

CROSS-REFERENCE TO RELATED APPLICATION

This application is a national phase application of International Application No. PCT/EP2004/009364, filed Aug. 20, 2004, which claims priority to German Patent Application No. 103 38 733.1, filed Aug. 22, 2003. The disclosures of these applications are hereby incorporated by reference in their entirety.

The present invention relates to fusion polypeptides, comprising at least two peptides. One peptide comprises from 3 to 30 amino acids and permits the fusion polypeptide to be bound selectively to endothelial cells in tumor vessels. The other peptide consists of the tissue factor (TF) or a fragment thereof, the tissue factor and the fragment being characterized in that they are able to activate blood clotting upon binding of the fusion polypeptide to endothelial cells in tumor vessels. The peptides can be joined together either directly or via a linker having up to 15 amino acids. The invention further relates to the use of these fusion proteins in antivascular therapy of neoplastic diseases and to their use in the production of a drug for the treatment of neoplastic diseases.

BACKGROUND OF THE INVENTION

Adequate neovascularization is a prerequisite for progressive tumor growth (1). Neoangiogenesis is required in particular for maintaining expansive tumor growth, since only sufficient oxygenation will ensure the supply with nutrients to and removal of tumor degradation products from the tumor.

In the prior art directed to tumor treatment antivascular therapeutic strategies have been developed, which are aimed at destruction of the tumor blood vessels and associated tumor infarction, in addition to anti-angiogenic therapeutic strategies, which attack the complex process of growth and differentiation of blood vessels.

A precondition for these strategies is identification of target structures in the vascular endothelium of the tumor that do not occur on resting endothelial cells in normal tissue. These specific target structures could be utilized in order to apply cytostatics or certain toxins to the vascular endothelial cells of the tumor to a lesser extent to the tumor cells themselves. Target structures that can be used for this purpose are bFGF (basic fibroblast growth factor), VEGF (vascular endothelial growth factor) and VEGFR-2 (VEGF receptor 2), endoglin, endosialin, a fibronectin isoform (ED-B domains), the integrins $\alpha_v\beta_3$, $\alpha_v\beta_5$, $\alpha_1\beta_1$, and $\alpha_1\beta_2$, aminopeptidase N, NG2 proteoglycan and the matrix metalloproteinases 2 and 9 (MMP 2 and 9) (2-13). For example, Arap et al. (8) coupled peptides that bind alpha1-integrins specifically, to an active substance that was being used in the state of the art for chemotherapy (doxorubicin). It was demonstrated in an animal model that the antineoplastic effect of doxorubicin could be improved by coupling to the peptides.

An alternative antivascular therapeutic approach comprises selective activation of blood clotting in tumor vessels, in order to induce tumor necrosis. For example, a bispecific F(ab')2 antibody fragment was produced, which is directed against truncated tissue factor (tTF) and an MHC class II antigen. After experimental induction of the antigen in tumor endothelial cells, an antivascular therapy could be demonstrated by administering the antibody in a murine neuroblastoma model (14). In a second study by the same team, an immunoconjugate was used, which couples tTF selectively to a naturally occurring marker of the tumor vessel endothelium, VCAM-1 (vascular cell adhesion molecule-1) (15).

In a very similar approach, an antibody fragment (scFv), which is specific for the oncofetal ED-B domain, was fused with tTF. The fusion proteins generated, scFv-tTF, led to a complete and selective infarction in various tumors in the mouse model (16).

Alternatively, tTF was coupled to an inhibitor of the prostate-specific membrane antigen (17). This fusion protein induced selective infarction necrosis in a rat prostate model after intravenous administration. Administering this fusion protein in combination with a cytotoxic substance (doxorubicin) at low dose resulted in massive tumor regression and even complete tumor eradication (17). Other tTF fusion proteins, consisting of antibody fragments against VEGFR (VEGF receptor), endoglin and VCAM-1, have been described recently (18).

However, the molecules produced for antivascular tumor therapy in the state of the art have drawbacks. In particular it has to be assumed that these molecules are immunogenic owing to their size. Treatment of mammals with these molecules will therefore trigger an immune reaction against the molecules, so that repeated administration of the molecules becomes impossible.

The size of the coupling partner, by means of which the peptide portion, which can activate blood clotting, is to be directed onto the tumor tissue, may further cause steric hindrance to a formation of the macromolecular factor VIIa/FX enzyme-substrate complex, which is important for blood clotting. Formation of the complex can also be hampered when the peptide capable of activating blood clotting has an altered conformation owing to the relatively large fusion partners.

In the state of the art (WO 03/035688), fusion polypeptides are also known wherein a selective binding domain, e.g. a domain of fibronectin that binds to integrins, e.g. which comprises RGD peptides, or the D-β-E dipeptide, which binds to PSMA (prostate-specific membrane antigen), is coupled to the N-terminus of a tissue factor polypeptide. Although an amidolytic and proteolytic effect was demonstrated in vitro, the constructs, even in combination with factor VIIa, only displayed extremely weak anti-tumor effect in vivo. The animals only survived longer in combination with doxycycline.

Hu et al. (46) describe various fusion proteins and use thereof for the production of thromboses in tumor vessels, including a fusion protein from an oligopeptide with 9 amino acids, containing the RGD sequence, which was coupled to the truncated form of the tissue factor. Again, the RGD peptides were linked to the N-terminus of tTF to obtain RGD-tTF. Functional analysis showed that the fusion protein containing RGD did not produce any significant inhibition of tumor growth.

The constructs known in the state of the art were thus constructed in such a manner that the selective binding domain was linked to the N-terminus of the tissue factor polypeptide. It was even emphasized that this structure must be chosen because the N-terminus, on the basis of structural models, was considered to be an especially favorable site for linkage, which would not inhibit the initiation of thrombosis.

SUMMARY OF THE INVENTION

In view of this prior art, the problem therefore resides in providing alternative thrombogenic substances, which can effectively inhibit tumor growth in vivo.

This problem is now solved by fusion polypeptides, which comprise a peptide of 3-30 amino acids, which permits the fusion polypeptide to be bound selectively to tumor vessel endothelial cells, and the tissue factor (TF) or a fragment thereof, the tissue factor and the fragment being characterized in that they are able to activate blood clotting when the fusion polypeptide binds to tumor vessel endothelial cells, these peptides being coupled to one another either directly or via a linker having up to 15 amino acids. The peptide, which enables the fusion polypeptide to be bound selectively to tumor vessel endothelial cells, is coupled to the C-terminus of the peptide, which can activate blood clotting when the fusion polypeptide binds to tumor vessel endothelial cells. The present invention further relates to pharmaceutical compositions containing corresponding fusion polypeptides, and use thereof for the treatment of tumors.

DESCRIPTION OF THE FIGURES

FIG. 12: Amino acid sequence of human tissue factor (TF) (SEQ ID NO:1).

FIG. 13: Amino acid sequence of the truncated human tissue factor $tTF_{1-218}$ (SEQ ID NO:2) (also designated tTF for short within the scope of the present application).

FIG. 14: Amino acid sequence of the fusion polypeptide tTF-GRGDSP (SEQ ID NO:3) (also abbreviated to tTF-RGD).

FIG. 15: Amino acid sequence of the fusion polypeptide tTF-GNGRAHA (SEQ ID NO:4) (also abbreviated to tTF-NGR).

FIG. 16: Amino acid sequence of the fusion polypeptide tTF-GALNGRSHAG (SEQ ID NO:5).

FIG. 17: Amino acid sequence of the fusion polypeptide tTF-GCNGRCG (SEQ ID NO:6) (also abbreviated to tTF-cycloNGR1).

FIG. 18: Amino acid sequence of the fusion polypeptide tTF-GCNGRCVSGCAGRC (SEQ ID NO:7) (also abbreviated to tTF-cycloNGR2).

FIG. 19: Amino acid sequence of the fusion polypeptide tTF-GCVLNGRMEC (SEQ ID NO:8) (also abbreviated to tTF-cycloNGR3).

FIG. 20: Nucleotide sequence of the truncated human tissue factor $tTF_{1-218}$ (SEQ ID NO:9) (also designated tTF for short within the scope of the present application).

FIG. 21: Nucleotide sequence of the fusion polypeptide tTF-GRGDSP (SEQ ID NO:10) (also abbreviated to tTF-RGD).

FIG. 22: Nucleotide sequence of the fusion polypeptide tTF-GNGRAHA (SEQ ID NO:11) (also abbreviated to tTF-NGR).

FIG. 23: Nucleotide sequence of the fusion polypeptide tTF-GALNGRSHAG (SEQ ID NO:12).

FIG. 24: Nucleotide sequence of the fusion polypeptide tTF-GCNGRCG (SEQ ID NO:13) (also abbreviated to tTF-cycloNGR1).

FIG. 25: Nucleotide sequence of the fusion polypeptide tTF-GCNGRCVSGCAGRC (SEQ ID NO:14) (also abbreviated to tTF-cycloNGR2).

FIG. 26: Nucleotide sequence of the fusion polypeptide tTF-GCVLNGRMEC (SEQ ID NO:15) (also abbreviated to tTF-cycloNGR3).

FIG. 27: Nucleotide sequence of the oligonucleotides for production of tTF$_{1-218}$ (SEQ ID NO:2).

A: 5'-primer (SEQ ID NO:16); B: 3'-primer (SEQ ID NO:17).

FIG. 28: Nucleotide sequence of the oligonucleotides for production of tTF-GRGDSP (SEQ ID NO:3).

A: 5'-primer (SEQ ID NO:18); B: 3'-primer (SEQ ID NO:19).

FIG. 29: Nucleotide sequence of the oligonucleotides for production of tTF-GNGRAHA (SEQ ID NO:4).

A: 5'-primer (SEQ ID NO:20); B: 3'-primer (SEQ ID NO:21).

FIG. 30: Nucleotide sequence of the oligonucleotides for production of tTF-GCNGRCG (SEQ ID NO:6).

A: 5'-primer (SEQ ID NO:22); B: 3'-primer (SEQ ID NO:23).

FIG. 31: Nucleotide sequence of the oligonucleotides for production of tTF-GCNGRCVSGCAGRC (SEQ ID NO:7).

A: 5'-primer (SEQ ID NO:24); B: 3'-primer (SEQ ID NO:25).

FIG. 32: Nucleotide sequence of the oligonucleotides for production of tTF-GCVLNGRMEC (SEQ ID NO:8).

A: 5'-primer (SEQ ID NO:26); B: 3'-primer (SEQ ID NO:27).

FIG. 33: Nucleotide sequence of the oligonucleotides for production of tTF-GALNGRSHAG (SEQ ID NO:5).

A: 5'-primer (SEQ ID NO:28); B: 3'-primer (SEQ ID NO:29).

FIG. 34: a: Inhibition and partial remission of a human malignant melanoma (M21) growing as a xenograft in athymic nude mice by intravenous therapy with tTF fusion proteins (tTF-RGD, n=7) compared with the growth of the tumors with infusion of physiological saline solution (NaCl, n=9) or tTF (n=11). The vertical arrows indicate the times of the injections with the respective substances.

b: Inhibition of a human fibrosarcoma (HT1080) growing as a xenograft in athymic nude mice by intravenous therapy with tTF fusion proteins (tTF-RGD, n=12) compared with the growth of the tumors with infusion of physiological saline solution (NaCl, n=15) or tTF (n=14). The vertical arrows indicate the times of the injections with the respective substances.

c: Inhibition of a human lung carcinoma (CCL185) growing as a xenograft in athymic nude mice by intravenous therapy with tTF fusion proteins (tTF-RGD, n=11) compared with the growth of the tumors in infusion of physiological saline solution (NaCl, n=10) or tTF (n=5). The vertical arrows indicate the times of the injections with the respective substances. Statistical significance was investigated in each case with the Mann-Whitney test for independent groups, P values under 0.05 being regarded as significant. * shows the statistical significance of the difference between tTF-RGD and buffer.

Figure 35:

FIG. 35: Macrograph of a mouse bearing an M21 tumor at the end of treatment (day 7) with tTF-RGD fusion protein (A, C) or NaCl (B, D). The difference in size and the different appearance of the tTF-RGD-treated tumors, which in contrast to the apparently vital control tumor show clear signs of necrosis, are readily discernible.

Figure 36:
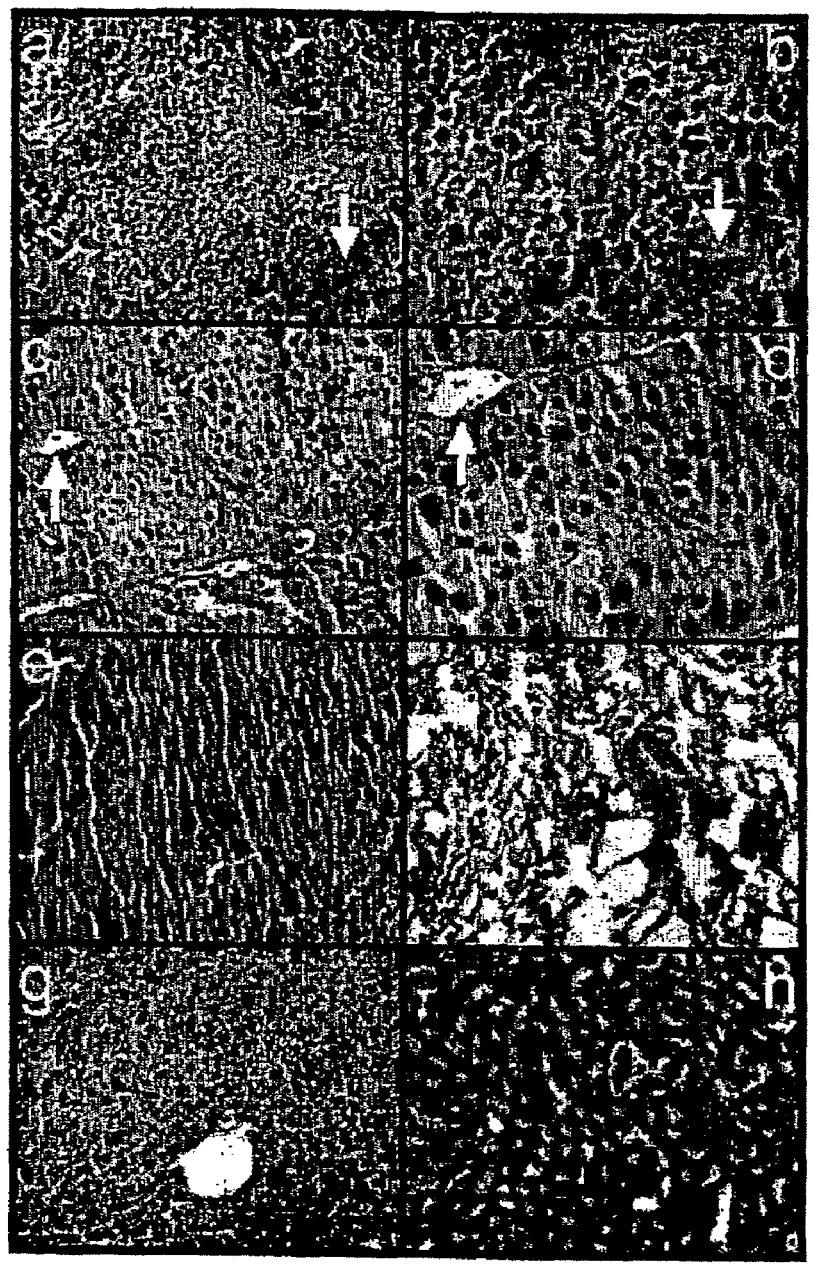

FIG. 36: H-E staining of tumors and organs of mice treated with tTF-RGD and physiological saline solution Severe thrombosis and necrosis of tumor cells was observed in animals treated with tTF-RGD (A: 200×, B: 400×). Arrows show examples of thromboses in blood vessels of the tumor. No obvious thrombosis or necrosis occurred in animals treated with saline (C: 200×, D: 400×). Arrows show intact blood vessels of the tumor with some erythrocytes. Heart (E), lung (F), liver (G) and kidney (H) of the animals treated with tTF-RGD did not show any visible thrombosis or necrosis.

Figure 37:
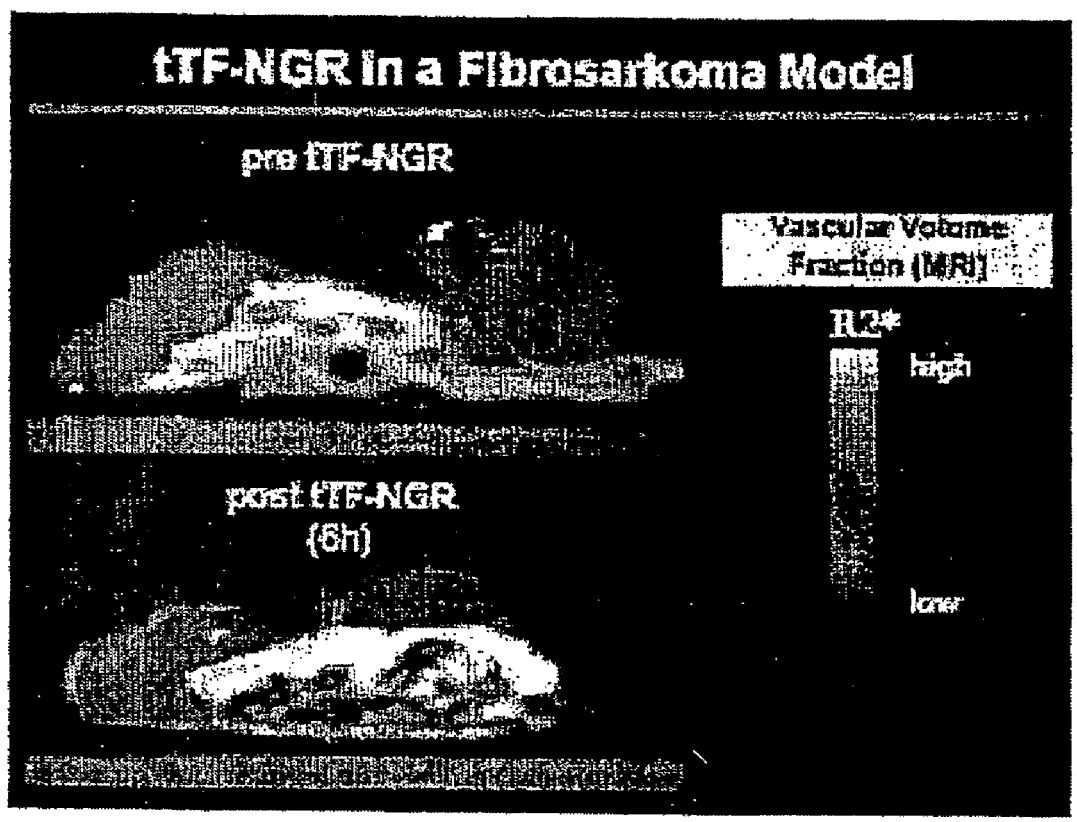

FIG. 37: Action of tTF-NGR in a fibrosarcoma model

Mice bearing a fibrosarcoma (HT1080) were investigated by magnetic resonance imaging (MRI) without (pre tTF-NGR) and 6 hours after (post tTF-NGR) i.v. administration of tTF-NGR. The high or low vascular volume fraction is shown.

DETAILED DESCRIPTION OF THE INVENTION

The problems observed in the prior art were now overcome by fusion polypeptides, which comprise the following peptides:

a) a peptide of 3 to 30 amino acids capable of selectively binding the fusion polypeptide to tumor vessel endothelial cells; and b) a tissue factor (TF) or a fragment thereof, the tissue factor and the fragment being characterized in that they are able to activate blood clotting when the fusion polypeptide binds to tumor vessel endothelial cells, wherein the peptides a) and b) are coupled to one another either directly or via a linker having up to 15 amino acids, characterized in that the peptide capable of selectively binding the fusion polypeptide to tumor vessel endothelial cells is coupled to the C-terminus of the peptide capable of activating blood clotting upon binding of the fusion polypeptide to tumor vessel endothelial cells. The present invention further relates to drugs containing corresponding fusion polypeptides and the use thereof for the treatment of tumors.

In addition to sequences a) and b), the fusion polypeptides according to the invention may comprise additional sequences, provided these do not have an adverse effect on the steric conformation of the fusion polypeptide and do not hamper the formation of the enzyme-substrate complex that triggers blood clotting. The fusion polypeptides according to the invention may for example contain sequences of a His-Tag, which simplify the recombinant expression and purification of the peptide (cf. Examples). The presence of these sequences is not necessary, however. According to a preferred embodiment of the invention, the fusion polypeptide therefore comprises:

a) a peptide of 3 to 30 amino acids capable of selectively binding the fusion polypeptide to tumor vessel endothelial cells; and b) a tissue factor (TF) or a fragment thereof, the tissue factor and the fragment being characterized in that they are able to activate blood clotting when the fusion polypeptide binds to tumor vessel endothelial cells, wherein the peptides a) and b) are coupled to one another either directly or via a linker having up to 15 amino acids. According to a particularly preferred embodiment of the invention, the fusion polypeptide comprises:

a) a peptide of 3 to 30 amino acids capable of selectively binding the fusion polypeptide to tumor vessel endothelial cells; and b) a tissue factor (TF) or a fragment thereof, the tissue factor and the fragment being characterized in that they are able to activate blood clotting when the fusion polypeptide binds to tumor vessel endothelial cells, wherein the peptides a) and b) are coupled to one another.

According to the invention it was surprisingly shown, that fusion polypeptides from a particularly small peptide capable of selectively binding the fusion polypeptide to tumor vessel endothelial cells, and a peptide capable of activating blood clotting when the fusion polypeptide binds to tumor vessel endothelial cells, are especially advantageous for antivascular tumor therapy. The small size of the polypeptide which permits binding to tumor vessel endothelial cells improves the orientation of the fusion protein to the phospholipid membrane of the endothelial cell. Formation of the enzyme/substrate complex that is essential for blood clotting is not sterically hindered and the tissue factor TF, which can activate blood clotting, is not subjected to a change of conformation.

According to a preferred embodiment of the present invention, the peptide capable of activating blood clotting when the fusion polypeptide binds to tumor vessel endothelial cells is the tissue factor TF with the amino acid sequence shown in SEQ ID NO:1 (FIG. 12). The invention further comprises tissue factor sequences having an amino acid homology of at least 70% or at least 80% to SEQ ID NO:1 (FIG. 12), sequences with a homology of at least 95% being especially preferred. The degree of homology is determined by writing the two sequences one above the other, four gaps on a length of 100 amino acids being possible, to achieve maximum possible agreement of the sequences being compared (cf. Dayhoff, Atlas of Protein Sequence and Structure, 5, 124, 1972). Then the percentage of the amino acid residues of the shorter of the two amino acid chains is determined, which stands opposite to identical amino acid residues on the other chain.

The peptide capable of activating blood clotting in tumor vessels when the fusion polypeptide binds to tumor vessel endothelial cells can moreover be a fragment of the tissue factor TF or a fragment of a sequence homologous to TF. Preferably the fragment has the sequence shown in SEQ ID NO:2 (FIG. 13). The sequence ($tTF_{1-218}$ or tTF for short) shown in SEQ ID NO:2 (FIG. 13) comprises the N-terminal 218 amino acids of TF. Moreover, according to the invention it is also possible to use fragments of tTF that lack several amino acids at the N-terminus or C-terminus, relative to tTF. For example, it is possible to use fragments that lack up to 10 amino acids at the N-terminus ($tTF_{11-218}$). Furthermore, fragments can be used that lack up to 8 amino acids at the C-terminus ($tTF_{1-210}$), such as ($tTF_{1-214}$).

The present invention relates to fusion polypeptides wherein the peptide capable of selectively binding to the endothelial cells of tumor vessels is coupled to the C-terminus of the peptide capable of activating blood clotting. According to the invention, the term "tumor vessel endothelial cells" and the term "endothelial cells in tumor vessels" are used to refer to cells covering the blood vessels of a tumor. It was established according to the invention that the above arrangement ensures orientation of the fusion protein perpendicularly to the phospholipid membrane of the endothelial cell, which is especially advantageous for triggering blood clotting. This orientation corresponds to the natural orientation of the TF during induction of blood clotting. As shown in FIG. 3, very similar Michaelis-Menten kinetics are found with respect to activation of factor X by FVIIa/$tTF_{1-218}$ or FVIIa/$tTF_{1-218}$ fusion proteins for all constructs produced in this way. In the prior art, in contrast, the peptide which activates clotting was coupled to the C-terminus of the targeting molecule (cf. (16)). The fusion polypeptides according to the invention thus differ fundamentally from the peptides used in the prior art.

The peptide capable of selectively binding the fusion polypeptide to tumor vessel endothelial cells can be any peptide which has a length of 3-30 amino acids and binds tumor vessel endothelial cells with high specificity. Corresponding peptides can be isolated from peptide libraries by methods that are usual in the state of the art. They can have a linear or cyclic structure, depending on the peptide library that is chosen.

According to one embodiment of the present invention, the peptides that permit selective binding of the fusion polypeptide to tumor vessel endothelial cells comprise the amino acid sequence RGD or NGR. Both sequences were known in the prior art for their specific binding to integrins, especially $\alpha_v\beta_3$ and $\alpha_v\beta_5$ integrins (RGD peptides), and as cell adhesion motifs (NGR peptides) (cf. (8)). According to the invention it was shown, surprisingly, that these peptides are especially suitable to be part of a fusion polypeptide, the other part of which is a peptide capable of activating blood clotting in tumors when the fusion polypeptide binds to tumor vessel endothelial cells.

Especially advantageous effects were obtained with the linear peptides with the sequences GRGDSP (SEQ ID NO:33), GNGRAHA (SEQ ID NO:34) and GALNGRSHAG (SEQ ID NO:35) and the cyclic peptides with the sequences GCNGRCG (SEQ ID NO:36), GCNGRCVSGCAGRC (SEQ ID NO:37) and GCVLNGRMEC (SEQ ID NO:38). It was demonstrated that fusion polypeptides comprising these sequences and the sequence of the first 218 amino acids of human TF are highly suitable for antivascular tumor therapy. In particular, it was shown that these fusion polypeptides cause significant inhibition of tumor growth or reduce the size of tumors (see FIGS. 7 and 8). The observed induction of partial remission of the tumors (cf. FIG. 8) points to anticipation of positive results in human tumor therapy based on the high predictive power of the mouse model (42, 43, 44).

The invention further comprises fusion proteins with cyclic RGD peptides, since cyclization improves the affinity for integrins (as described for example in reference 21).

The present invention further relates to fusion polypeptides having one of the sequences shown in SEQ ID NO:3-8 (FIG. 14-19).

According to another embodiment, the present invention relates to nucleic acids encoding a fusion polypeptide, as described above. Corresponding nucleic acids can, for example, have one of the sequences shown in SEQ ID NO:10-15 (FIG. 21-26).

In yet another aspect, the present invention relates to vectors comprising one of the aforementioned nucleic acids. Corresponding vectors usually also comprise regulatory sequences for expression of the nucleic acid. Said vectors are comprehensively described in the prior art and are available commercially from a large number of companies.

In a further embodiment, the present invention relates to cells comprising one of the aforesaid nucleic acids or vectors.

The cells are generally used for expression of the nucleic acid and recombinant production of the fusion polypeptides according to the invention. A large number of cells may find application for this purpose, including *E. coli*, yeast cells and animal cell lines, such as CHO- or COS-cells. Appropriate cells and the use thereof are described comprehensively in the prior art.

The polypeptides of the invention according to claim 1 can further be produced by other suitable methods, for example by chemical coupling of individual peptides. Thus, individual peptides can be produced by methods that are conventional in the state of the art, e.g. by chemical synthesis or by heterologous expression, and are then joined together by coupling.

Finally, the present invention also relates to pharmaceutical compositions comprising the fusion polypeptides, nucleic acids, vectors or cells described above. The pharmaceutical compositions may further comprise pharmaceutically compatible carriers, excipients or adjuvants. Moreover, the polypeptides in said pharmaceutical composition may be present in a modified state, e.g. pegylated, i.e. coupled to a polyethylene glycol molecule.

The fusion polypeptides according to the invention or pharmaceutical compositions containing these fusion polypeptides may be used for the treatment of neoplastic diseases, and especially for antivascular tumor therapy. Neoplastic diseases that may be considered for treatment with the aid of the fusion polypeptides according to the invention or pharmaceutical compositions containing these fusion polypeptides include for example bronchial carcinomas and other tumors of the thorax and mediastinum, breast cancers and other gynecological tumors, colorectal carcinomas, pancreatic carcinomas and other tumors of the gastrointestinal tract, malignant melanomas and other skin tumors, tumors in the head and neck region, prostate carcinomas and other urogenital tumors, sarcomas, endocrine-active tumors, leukemias and Myelodysplastic Syndromes and Hodgkin lymphomas and non-Hodgkin lymphomas.

Further, benign tumors, for example hemangiomas, and neovascularization in diabetic retinopathy, can also be treated.

Apart from intravenous administration, subcutaneous and intraperitoneal administration of the fusion polypeptides or pharmaceutical compositions is also possible. By packaging in pharmaceutical vehicles, which prevent cleavage of the fusion polypeptides in the gastrointestinal tract, the fusion polypeptides or pharmaceutical compositions may also be administered orally.

It may further be advantageous to combine administration of the fusion polypeptides according to the invention with other therapeutic approaches, e.g. cytotoxic chemotherapy or irradiation. Combination with other active substances, e.g. combination with factor VIIa or doxycycline, is also possible, but preferably combination of the polypeptide according to the invention with factor VIIa or doxycycline is not necessary.

The invention is described in more detail on the basis of the following examples:

EXAMPLES

Example 1

Expression and Purification of tTF and tTF Fusion Proteins

The cDNA coding for the N-terminal 218 amino acids of tissue factor TF (designated as tTF hereinafter) was synthesized by the polymerase chain reaction (PCR) using the primers shown in SEQ ID NO:16 and SEQ ID NO:17 (FIG. 27) and cloned into the expression vector pET-30a(+) (Novagen). The recombinant plasmids were transformed in *E. coli* (BL21), expressed and purified (Qiagen Plasmid Kit).

Along with the truncated tissue factor tTF, tTF peptide fusion proteins were constructed, wherein the targeting peptides are first bound to the carboxyl terminal end of the soluble tissue factor tTF. The following linear fusion proteins were constructed:

tTF-GRGDSP (SEQ ID NO:3; FIG. 14; designated tTF-RGD hereinafter; the PCR primers SEQ ID NO:18 and SEQ ID NO:19 (FIG. 28) were used);

tTF-GNGRAHA (SEQ ID NO:4; FIG. 15; designated tTF-NGR hereinafter; the PCR primers SEQ ID NO:20 and SEQ ID NO:21 (FIG. 29) were used);

tTF-GALNGRSHAG (SEQ ID NO:5; FIG. 16; the PCR primers SEQ ID NO:28 and SEQ ID NO:29 (FIG. 33) were used);

In addition, the following cyclic fusion proteins were synthesized:

tTF-GCNGRCG (SEQ ID NO:6; FIG. 17; designated tTF-cycloNGR1 hereinafter; the PCR primers SEQ ID NO:22 and SEQ ID NO:23 (FIG. 30) were used);

tTF-GCNGRCVSGCAGRC (SEQ ID NO:7; FIG. 18; designated tTF-cycloNGR2 hereinafter; the PCR primers SEQ ID NO:24 and SEQ ID NO:25 (FIG. 31) were used);

tTF-GCVLNGRMEC (SEQ ID NO:8; FIG. 19; designated tTF-cycloNGR3 hereinafter; the PCR primers SEQ ID NO:26 and SEQ ID NO:27 (FIG. 32) were used)

All constructs (including tTF) were expressed in the pET30a(+) vector, which mediates the additional expression of an N-terminal affinity tag of 6 histidine residues and a few vector-coded amino acids. With the aid of this affinity tag, the constructs could be purified by affinity chromatography on a nickel-nitrilotriacetic acid column (Ni-NTA, Novagen). The affinity tag is shown in SEQ ID NO:30. SEQ ID NO:31 and SEQ ID NO:32 show, as examples, the complete amino acid sequences of tTF-GRGDSP with affinity tag (SEQ ID NO:31) and tTF-GNGRAHA with affinity tag (SEQ ID NO:32).

Figure 1:
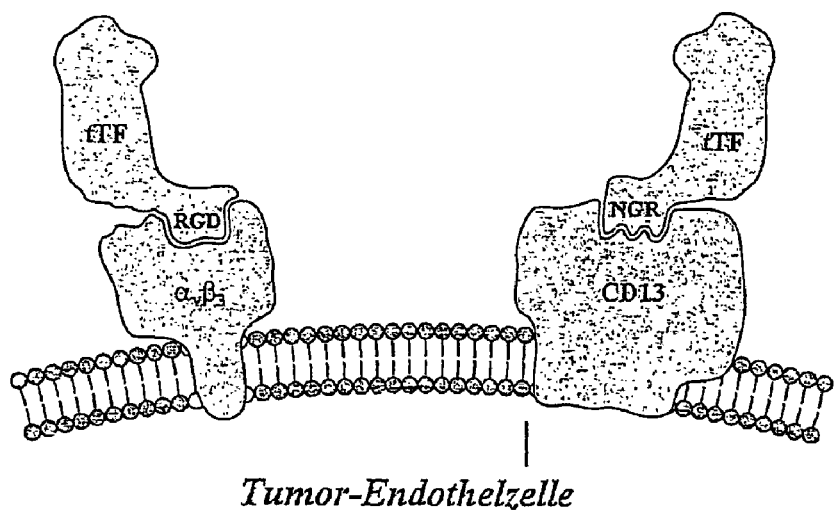
FIG. 1: Schematic presentation of binding of the tTF-RGD and tTF-NGR fusion proteins to $\alpha_v\beta_3$ and CD13. Tumor selectivity is achieved owing to the specificity of the RGD sequence for $\alpha_v\beta_3$-integrin and of the NGR sequence for CD13 (aminopeptidase N). These receptors are expressed selectively and specifically at high density on tumor endothelial cells, but not on resting endothelial cells in normal tissue (apart from a few exceptions). The representation of the fusion proteins is highly schematic and does not provide any information regarding the primary sequence.

The constructs were selected so that, on the basis of the known X-ray crystal structure of the tTF:FVIIa complex (19), vertical orientation of the tTF fusion protein to the phospholipid membrane of the endothelial cells is ensured, which corresponds to the orientation of the native TF. It was further taken into account that the structure selected should not result in the tTF causing any steric hindrance to interaction with FVIIa and the macromolecular substrate FX. Owing to the specificity of the RGD sequence for the $\alpha_v\beta_3$ integrin and of the NGR sequence for CD13 (aminopeptidase N), tumor selectivity is achieved, as these receptors are expressed selectively and specifically at high density on tumor endothelial cells but, apart from a few exceptions, not on resting endothelial cells in normal tissue (see FIG. 1).

tTF and the fusion proteins described tTF-RGD, tTF-NGR, tTF-GALNGRSHAG (SEQ ID NO:5) and tTF-cycloNGR1-3 were transformed and expressed in *E. coli* (BL21) by means of pET30a(+). Transformed, IPTG-induced *E. coli* BL21 DE3 were centrifuged and absorbed in 5-7 ml lysis buffer (10 mM Tris-HCl, pH 7.5; 150 mM NaCl; 1 mM $MgCl_2$; 10 µg/ml aprotinin; 2 mg/ml lysozyme)/g pellet and 20 µl Benzonase (Novagen) added. After 90 min incubation at room temperature (RT) and centrifugation at 12 000 g, 20 min, 4° C., the pellet was resuspended and homogenized by ultrasonic treatment in washing buffer (10 mM Tris/HCl, pH 7.5; 1 mM EDTA; 3% Triton X-100). Inclusion bodies were dissolved over night at RT in 2-4 ml/g pellet on denaturing buffer (6 M guanidinium chloride, 0.5 M NaCl, 20 mM NaH$_2$PO$_4$, 1 mM DTT). The supernatant from centrifugation (5000 g, 30 min, 4° C.) was filtered with a 0.22 µg filter. The constructs were purified until homogeneous on a nickel-nitrilotriacetic acid column (Ni-NTA, Novagen) via the additionally introduced His-Tag sequences of the construct. Purification and folding of the proteins were carried out with the His Bind Buffer Kit (Novagen). This was followed by dialysis against TBS buffer (20 mM Tris, 150 mM NaCl, pH 7.4).

Figure 2:
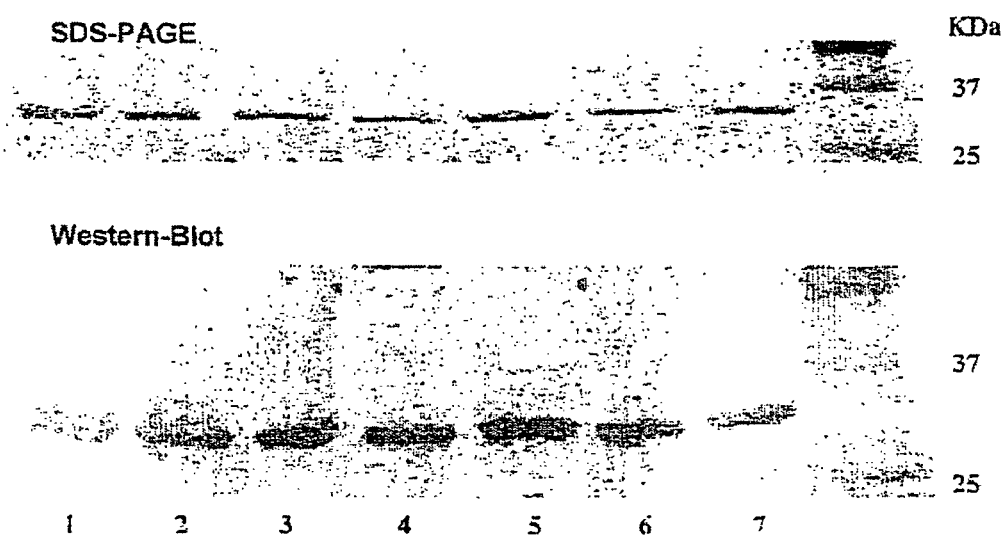
FIG. 2: SDS-PAGE and Western Blot analysis of recombinant $tTF_{1-218}$ (SEQ ID NO:2) and tTF fusion proteins. The purity of the tTF and of the tTF fusion proteins was checked by SDS-PAGE and staining with Coomassie Blue after extraction from E. coli (BL21 DE3) and refolding over a linear urea gradient (6M-1 M). Identity of the proteins was verified by Western blotting using a monoclonal anti-tissue-factor antibody (clone V1C7, American Diagnostics). Loading in the individual lanes: 1=tTF; 2=tTF-RGD; 3=tTF-NGR; 4=tTF-cycloNGR1 (SEQ ID NO:6); 5=tTF-cycloNGR2 (SEQ ID NO:7); 6=tTF-cycloNGR3 (SEQ ID NO: 8); 7=tTF-GALNGRSHAG (SEQ ID NO: 5); M=molecular weight marker.

The identity of the proteins was confirmed by SDS-PAGE, Western Blot and mass spectroscopy (see FIG. 2).

Example 2

Functional Characterization of tTF and tTF Fusion Proteins

Figure 3:
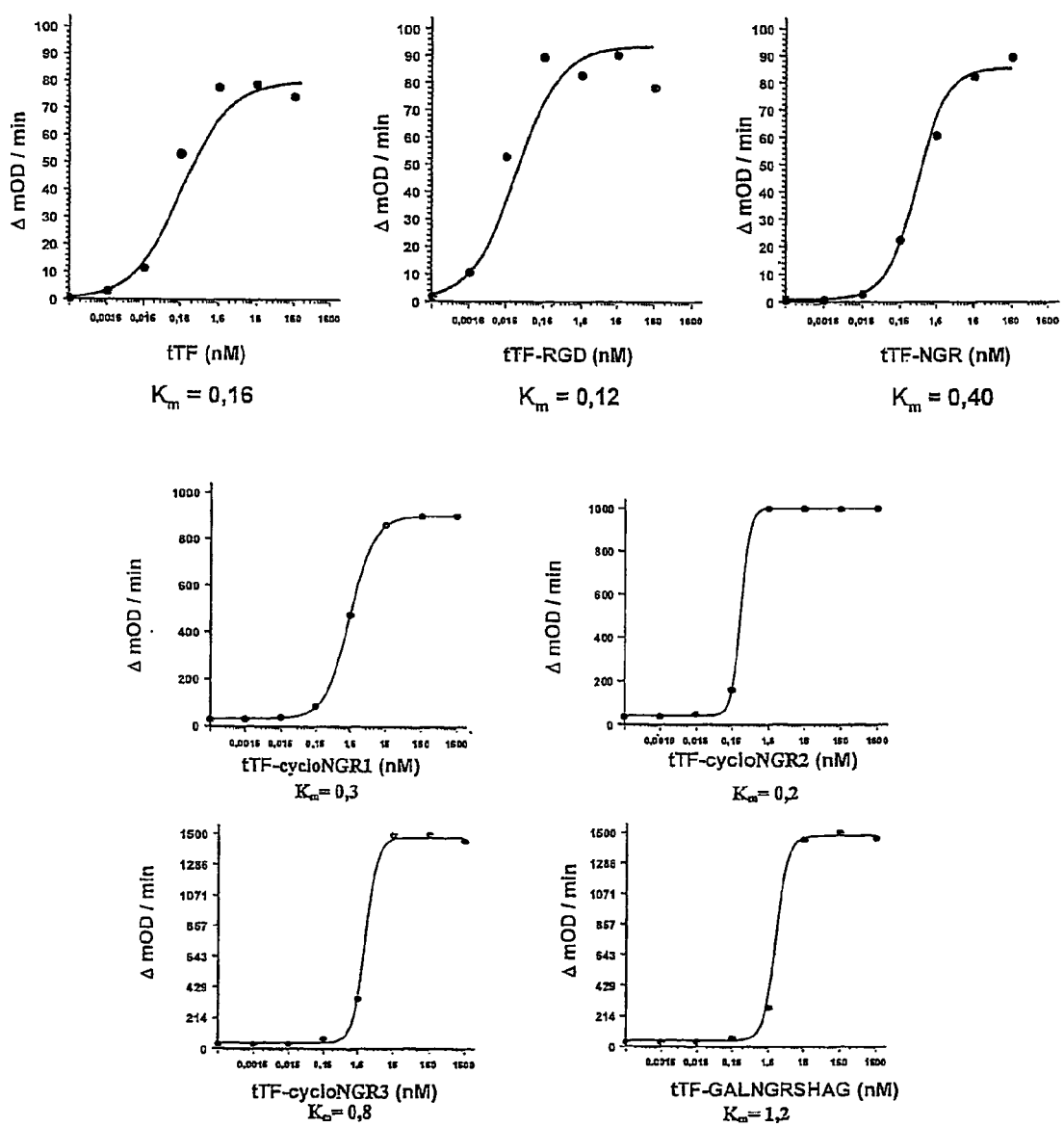
FIG. 3: Determination of the Michaelis constants (Km) for the activation of FX by FVIIa/$tTF_{1-218}$ or FVIIa/$tTF_{1-218}$ fusion proteins. The parameters of Michaelis-Menten kinetics were calculated using the method described by Ruf (45).

The functional activity of these fusion proteins with respect to cofactor activity in the activation of factor X to factor Xa via factor VIIa was demonstrated in vitro by Michaelis-Menten analyses. The ability of tTF and of the tTF fusion polypeptides to intensify the specific proteolytic activation of FX via FVIIa in the presence of phospholipids was determined in a slightly modified version of the method described by Ruf (45). For this, 20 µl of each of the following reagents was pipetted in microtiter plates: (a) 50 nM recombinant FVIIa (Novo-Nordisk) in TBS-BSA; (b) 0.16 nM-1.6 µM tTF/tTF fusion polypeptide in TBS-BSA; (c) 25 mM CaCl$_2$ and 500 µM phospholipid vesicle (phosphatidylcholine/phosphatidylserine, 70/30, M/M; Sigma). After 10 min incubation at room temperature, 20 µl of the natural substrate FX (Enzyme Research Laboratories) was added at a concentration of 5 µM. Then a sample was taken by pipette at one-minute intervals and the reaction was stopped by adding 100 mM EDTA solution. The amount of FXa that formed was measured by addition of the chromogenic substrate Spectrozyme FXa in a Microplate Reader by determining the change in absorption at 405 nm and the parameters for the Michaelis-Menten kinetics were analysed by the method described by Ruf. The results show that both tTF and the tTF fusion polypeptides are functionally active under these conditions (FIG. 3). The Michaelis constants (Km) found for the fusion polypeptides were in the range 0.12-1.2 nM (FIG. 3), and thus in the lower range that is published for tTF. It can therefore be assumed that the functional activity is unaffected by the fusing of tTF with the peptides.

Example 3

Binding of the tTF Fusion Proteins to $\alpha_v\beta_3$ In Vitro and In Vivo

Figure 4:
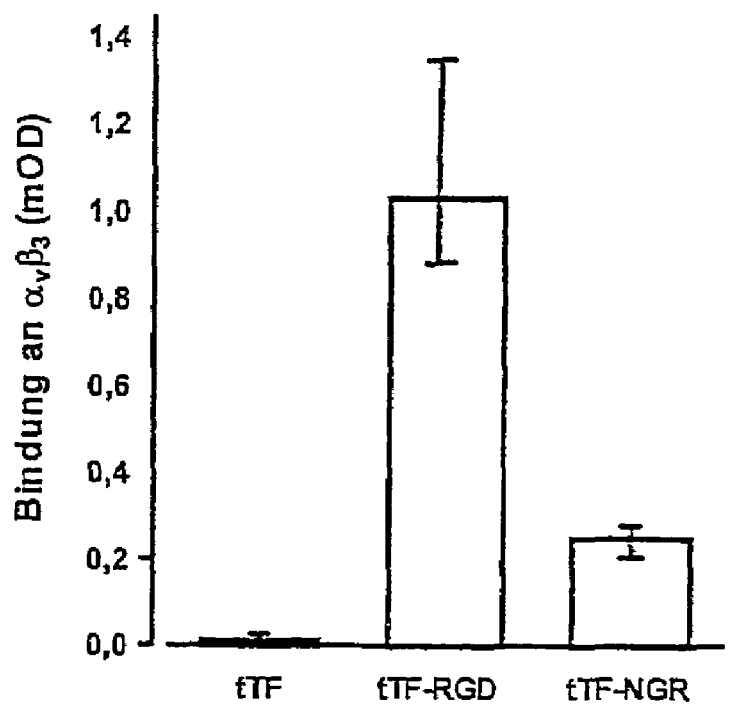
FIG. 4: Binding of tTF, tTF-RGD and tTF-NGR to integrin $\alpha_v\beta_3$. The binding of 0.1 μM tTF, tTF-RGD and tTF-NGR to immobilized $\alpha_v\beta_3$ was quantified with a polyclonal antibody against human TF (American Diagnostica) in an ELISA. The results are presented as median and interquartile range. The differences in binding between tTF-RGD and tTF or between tTF-NGR and tTF were statistically significant (p<0.001, Mann-Whitney test).
Figure 5:
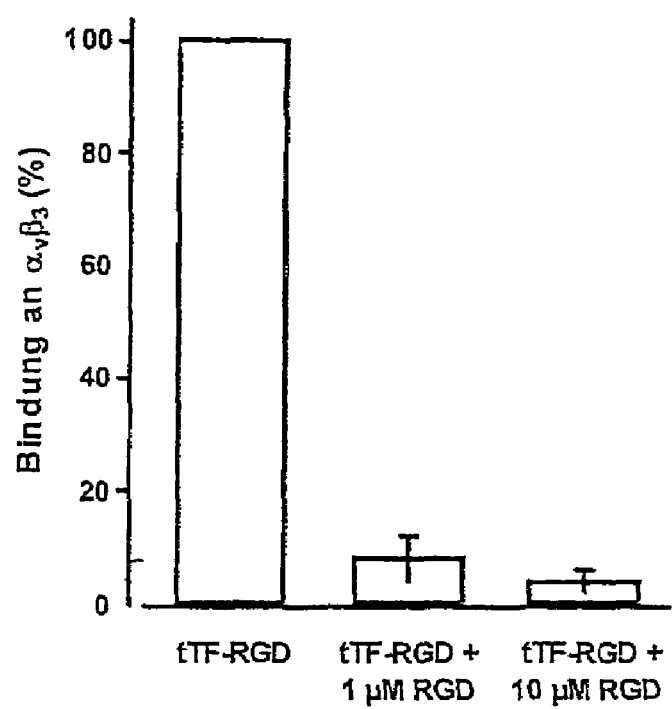
FIG. 5: Specificity of the binding of tTF-RGD to integrin $\alpha_v\beta_3$ The binding of tTF-RGD (0.1 μM) to immobilized $\alpha_v\beta_3$ was inhibited significantly by competitive inhibition with the synthetic peptide GRGDSP (SEQ ID NO:33) (1-10 μM) (p<0.001, Mann-Whitney test for both RGD peptide concentrations).

Binding of tTF-RGD and tTF-NGR to the $\alpha_v\beta_3$ integrin was demonstrated in an ELISA (Enzyme Linked Immunosorbent Assay), by immobilizing purified $\alpha_v\beta_3$ on microtiter plates (see FIG. 4). The specificity of the binding of tTF-RGD to $\alpha_v\beta_3$ was emphasized by the fact that the synthetic peptide with the sequence GRGDSP (SEQ ID NO:33) (from the company Gibco) competitively inhibits the binding of tTF-RGD to $\alpha_v\beta_3$ in this test system (see FIG. 5).

Next the specific binding of tTF-RGD to $\alpha_v\beta_3$ on endothelial cells was evaluated. For this, the differential binding of biotinylated tTF and tTF-RGD to endothelial cells in suspension was analysed by FACS (Fluorescence Activated Cell Sorting). The fact that all endothelial cells held in tissue culture are activated, i.e. express $\alpha_v\beta_3$ molecules, is utilized experimentally. This can be detected by various immunohistochemical methods. A cultivated endothelial cell thus corresponds, in relation to its expression pattern with respect to $\alpha_v\beta_3$ to a tumor endothelial cell. Accordingly, a cultivated endothelial cell can be used as a model system for the specific binding of substances to tumor endothelial cells and also permits predictions to be made concerning the expected toxicity.

Figure 6:
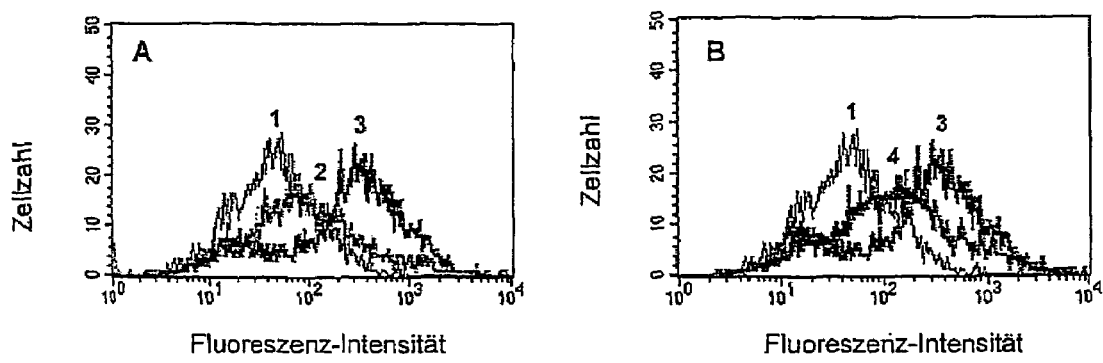
FIG. 6: Binding of tTF and tTF-RGD to human endothelial cells. A: FACS analysis of endothelial cells incubated with 0.1 μM tTF (2) or with 0.1 μM tTF-RGD (3) for 60 min at 4° C. B: A 75% reduction in binding was demonstrated by competitive inhibition of the tTF-RGD fusion protein with 1 μM GRGDSP (SEQ ID NO:33) (4). Curves 1 in A and B show the negative control.

Streptavidin-phycoerythrin was used as the detection method. The measured fluorescence intensity for tTF-RGD was higher by a factor of 8 than for tTF (FIG. 6A). Furthermore, the binding of 0.1 µM tTF-RGD to endothelial cells was lowered competitively by 75% by the administration of 1 µM of the synthetic peptide GRGDSP (SEQ ID NO:33) (FIG. 6B). This emphasizes the specificity of the binding of tTF-RGD to RGD-binding receptors on the endothelial cell surface like $\alpha_v\beta_3$.

Example 4

Antitumor Effects of the tTF Fusion Proteins in an Animal Model

Figure 7:
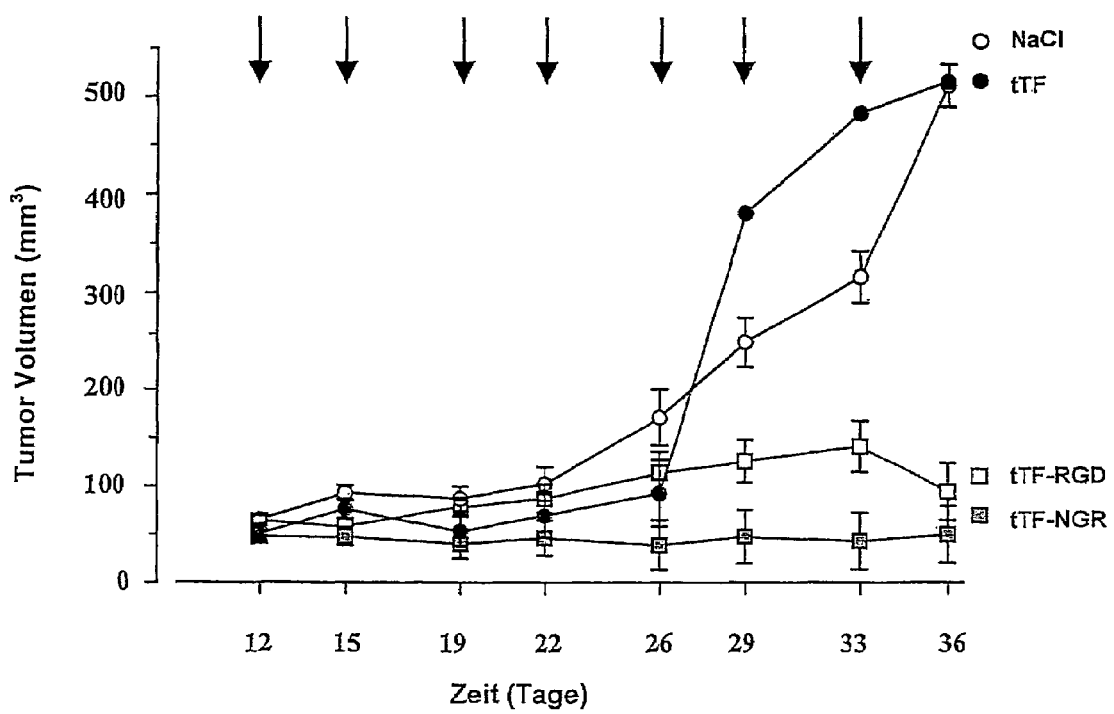
FIG. 7: Inhibition of a human lung carcinoma (CCL185) growing as a xenograft in athymic nude mice by intravenous therapy with tTF fusion proteins (tTF-RGD, n=6; tTF-NGR, n=6) compared with tumor growth with infusion of physiological saline solution (NaCl, n=8) or tTF (n=1). The vertical arrows indicate the times of injection with the respective substances.
Figure 8:
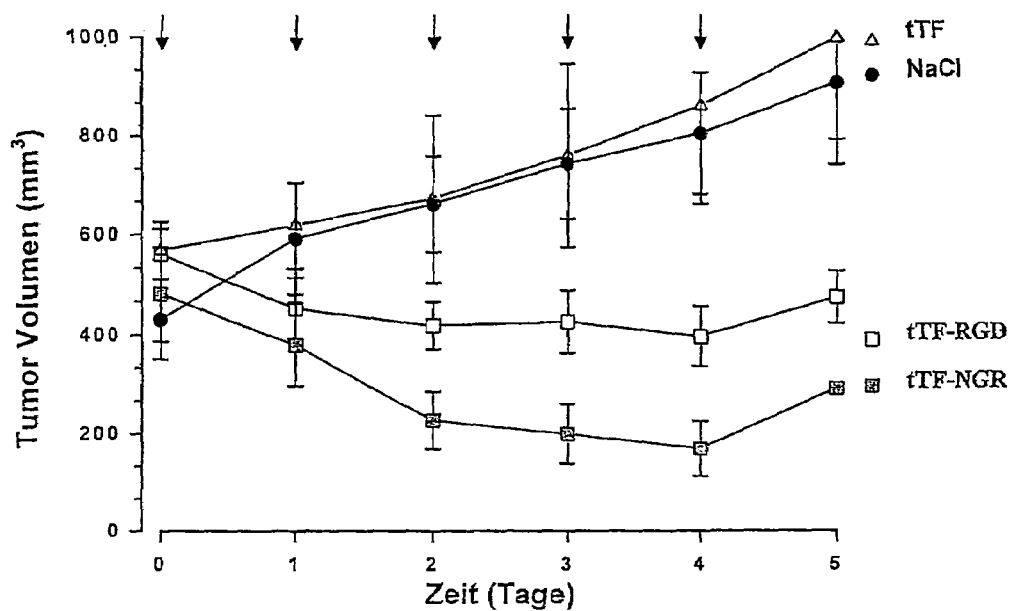
FIG. 8: Inhibition and partial remission of a human malignant melanoma (M21) growing as a xenograft in athymic nude mice by intravenous therapy with tTF fusion proteins (tTF-RGD, n=3; tTF-NGR, n=3) compared with tumor growth with infusion of physiological saline solution (NaCl, n=4) or tTF (n=4). The vertical arrows indicate the times of injection with the respective substances.

The tTF-RGD and tTF-NGR fusion proteins were evaluated with respect to their effects and side-effects on xenografts of human tumors in athymic nude mice. The models established in our laboratory were used for this (33, 34). The cell lines CCL185 (human adenocarcinoma of the lung) and M-21 (human melanoma) were injected subcutaneously into the flank of male BALB/c nude mice (9-12 weeks old). On attaining a tumor volume of about 50-100 mm$^3$ (CCL185) or 400-600 mm$^3$ (M–21), the mice were assigned to four groups at random. Group 1 received only physiological saline solution (NaCl), group 2 tTF, group 3 tTF-RGD, and group 4 tTF-NGR (in each case 1.5-2.0 mg/kg body weight (BW) of the protein). The injections were made in the caudal vein of the animals at intervals of 1-3 days (depending on the growth rate of the particular cell line). Considerable therapeutic activity of the fusion proteins was observed. The tumors of the mice treated with tTF-RGD or tTF-NGR fusion proteins were significantly inhibited in their growth or were reduced in size as far as partial remission in comparison with tTF or NaCl (see FIGS. 7 and 8).

Figure 9:
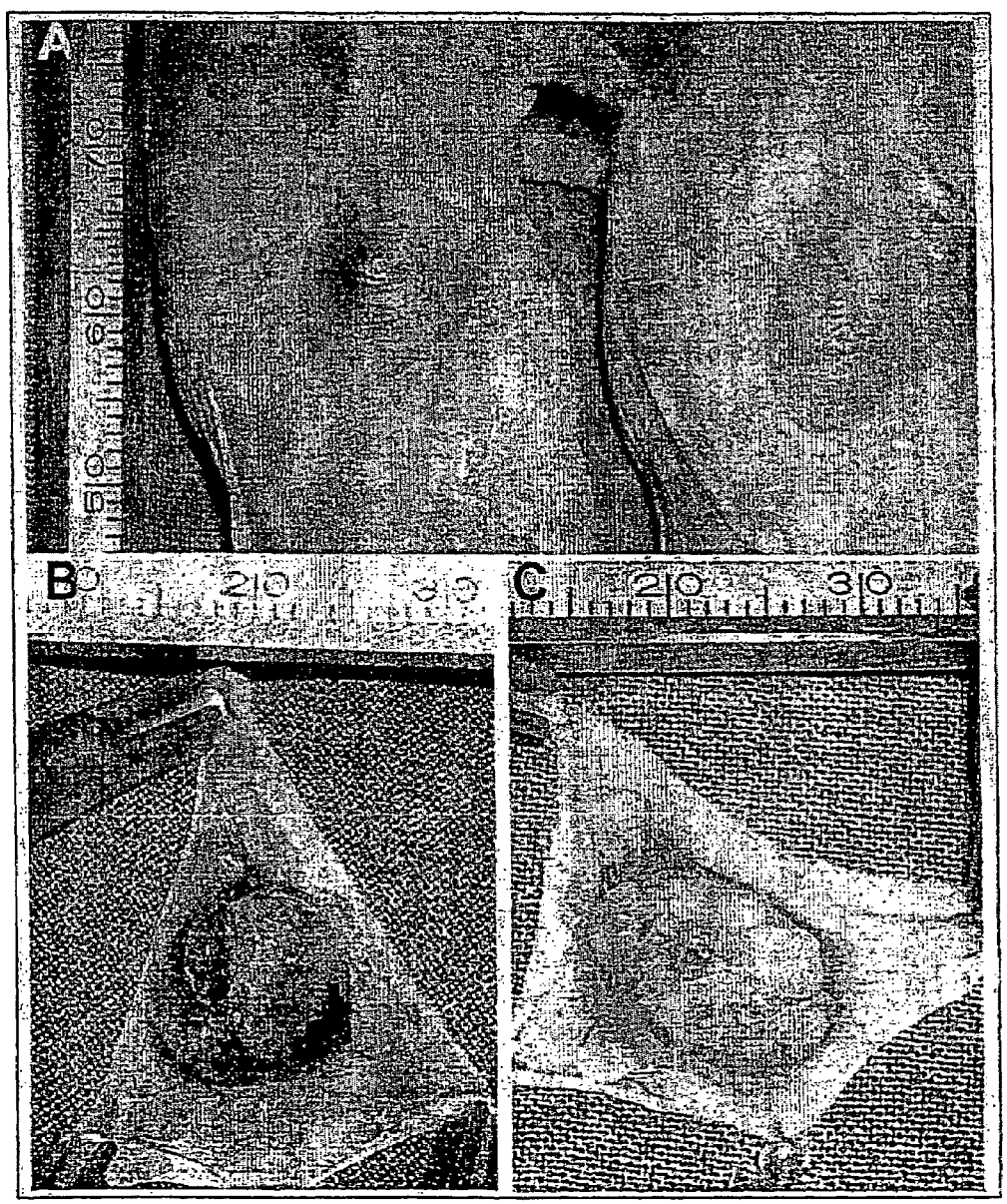
FIG. 9: Macroscopic in vivo photograph of a tumor-bearing mouse 20 min after injection of the tTF-NGR fusion protein (A, left half of the picture) or NaCl (A, right half of the picture). The macroscopic picture with bluish-livid coloration of the tumor after injection of tTF-NGR is indicative of tumor necrosis. After 60 min, the two mice were exsanguinated, the tumor was excised in toto and examined histologically. In B, we can see the hemorrhagic imbibition of the tumor treated with tTF-NGR as a sign of secondary hemorrhage as a result of incipient tumor necrosis. In contrast, the NaCl-treated tumor appears to be vital (C).
Figure 10:
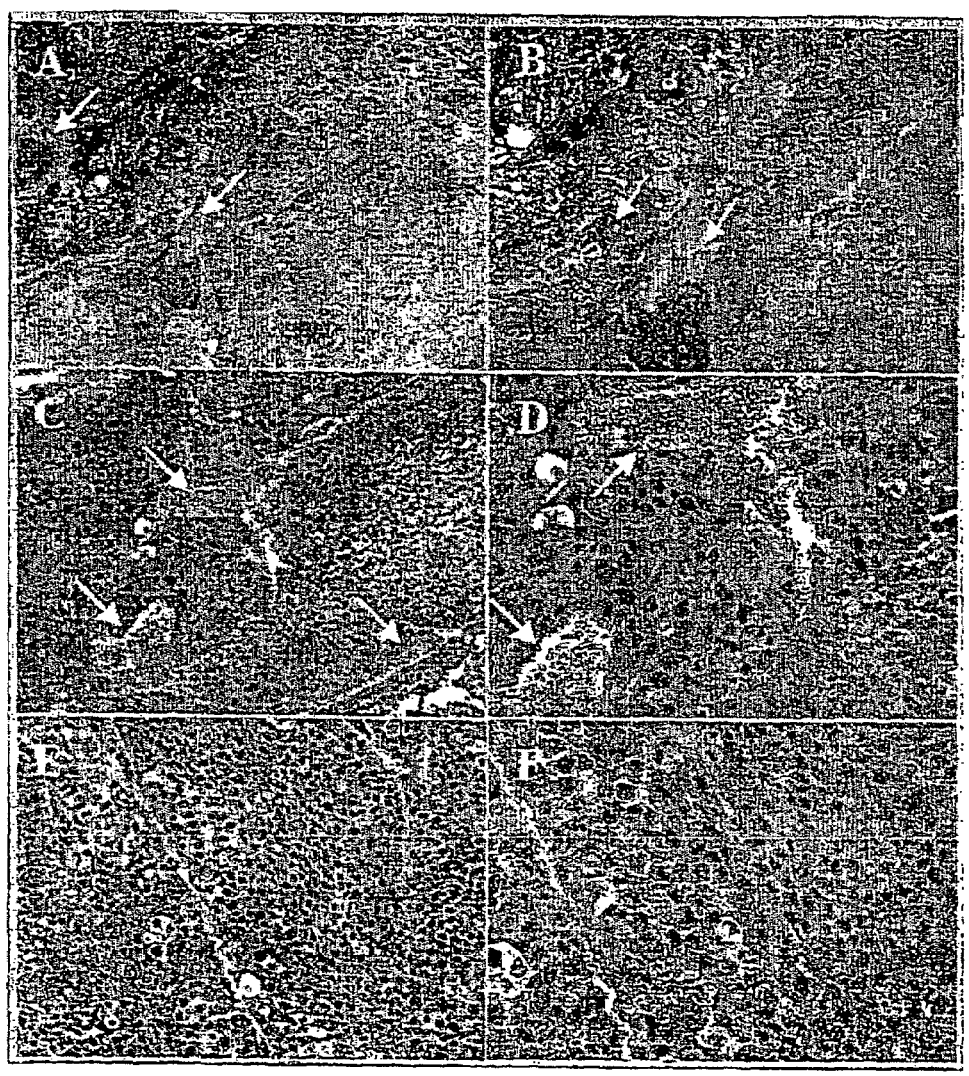
FIG. 10: Histology of the melanoma tumor 1 hour after intravenous injection of tTF-RGD (A and B), tTF-NGR (C and D) and common salt (E and F) in the caudal vein of the tumor-bearing nude mouse. In the tumors treated with the tTF fusion proteins, the blood vessels appear to be thrombolytically occluded (arrows). Extensive tumor necroses are observable in the supply region of the vessel occluded by a blood clot (A-D). The photographs are of representative areas of the tumors (A, C and E: 200× magnification, B, D and F 400× magnification; HE staining (staining described e.g. in H. C. Burck, Histologische Technik-Leitfaden für die Herstellung mikroskopischer Präparate in Unterricht und Praxis, 5th edition, Thieme Verlag, Stuttgart 1982, pages 109 ff.).
Figure 11:
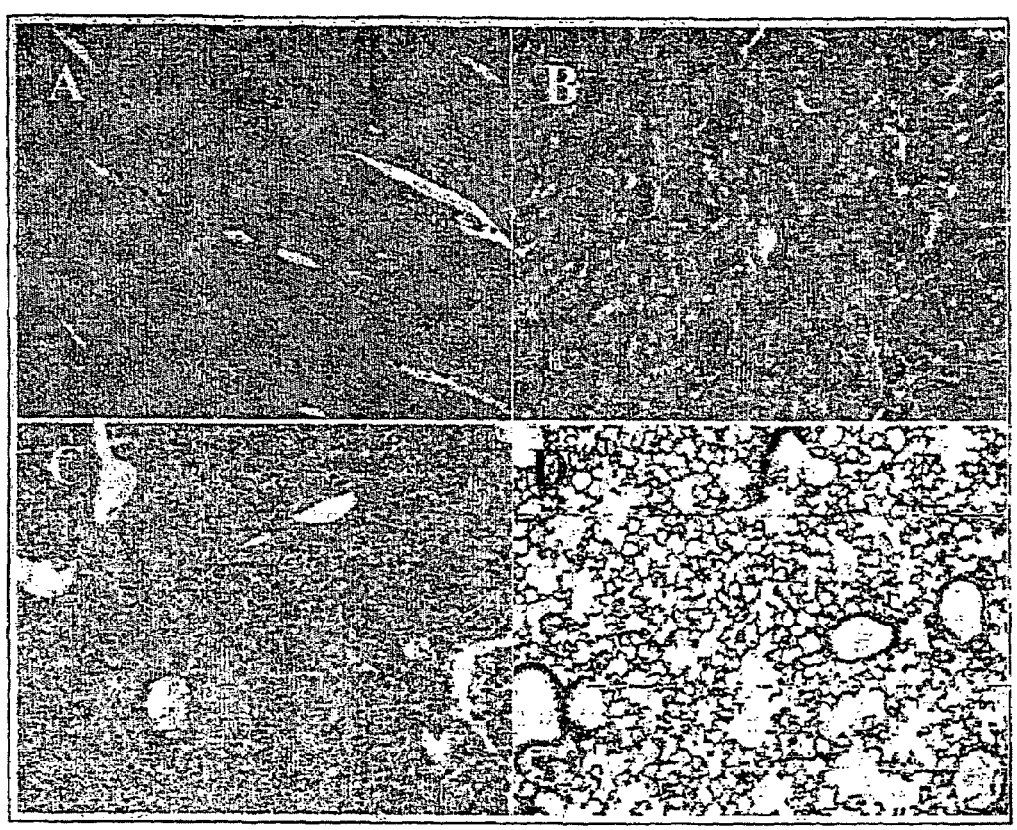
FIG. 11: Representative histologies of heart (A), kidney (B), liver (C) and lung (D) 1 hour after injection of 4 mg/kg BW tTF-NGR. Thromboses or necroses were not detected microscopically in any of these organs. (HE staining; 200× magnification).

To verify the mechanism of action of thrombosis induction in tumor vessels, the following experiment was carried out: the human melanoma cell line was injected into the flank of two male BALB/c nude mice. On attaining a tumor size of approx. 500 mm$^3$, 2.0 mg/kg BW tTF-NGR or NaCl was injected into the caudal vein. FIG. 9A shows an in-vivo macrograph of the tumor-bearing mouse 20 min after injection of the tTF-NGR fusion protein (left half of the picture) or NaCl (right half of the picture). The macroscopic picture with bluish-livid coloration of the tumor after injection of tTF-NGR indicates tumor necrosis. After 60 min the mice were exsanguinated, the tumor was excised in toto and investigated histologically. FIG. 9B shows the hemorrhagic imbibition of the tumor treated with tTF-NGR as a sign of secondary hemorrhage as a result of incipient tumor necrosis. In contrast, the tumor treated with NaCl appears to be vital (FIG. 9C).

Histological analysis of the melanoma tumor shows microscopically visible thrombus formation in the blood vessels (FIG. 10A-D). This finding verifies the suggested mechanism of anti-tumor effects of tTF-NGR, i.e. induction of thrombi in the blood vessels. The high selectivity of tTF-NGR for tumor blood vessels is demonstrated by the absence of histological detection of clotting and necrosis in normal tissue such as heart, kidney, liver and lung (FIG. 11A-D). Even repeated high doses of tTF-NGR (4 mg/kg BW) did not lead to any visible clot formation or organ toxicity.

Example 5

Antitumor Effects of the tTF Fusion Proteins in the HT1080 Tumor Animal Model

The antitumor activity of the tTF-RGD fusion protein was also investigated in BALB/c nude mice with fibrosarcomas (HT1080). These tumors grow rapidly and are well-vascularized. The results of two experiments are presented in Table 2 and FIG. 34. After the second injection of tTF-RGD, significant inhibition of growth of the HT1080 tumors was observed compared with control groups. This effect lasted until the end of the experiment on day 7 (P=0.021 for tTF-RGD relative to the buffer control (physiological saline solution), P=0.005 for tTF-RGD relative to tTF). As in the earlier experiments, partial regression of tumor volume was observed in this model.

TABLE 1

Effect of tTF-RGD on the growth of M21 tumors in mice

| Treatment | Mean tumor volume (mm³) | | P relative to buffer | P relative to tTF | n |
|---|---|---|---|---|---|
| | Day 0 | Day 7 | | | |
| Buffer | 590 ± 77 | 994 ± 140 | | ns | 9 |
| tTF | 558 ± 47 | 931 ± 147 | ns | | 11 |
| tTF-RGD | 585 ± 85 | 514 ± 81 | <0.01 | <0.05 | 7 | ns: not significant

TABLE 2

Effect of tTF-RGD on the growth of HT1080 tumors in mice

| Treatment | Mean tumor volume (mm³) | | P relative to buffer | P relative to tTF | n |
|---|---|---|---|---|---|
| | Day 0 | Day 7 | | | |
| Buffer | 1671 ± 296 | 2431 ± 559 | | ns | 15 |
| tTF | 1751 ± 269 | 2335 ± 398 | ns | | 14 |
| tTF-RGD | 1725 ± 197 | 1241 ± 122 | <0.05 | <0.01 | 12 | ns: not significant

TABLE 3

Effect of tTF-RGD on the growth of CCL185 tumors in mice

| Treatment | Mean tumor volume (mm³) | | P relative to buffer | P relative to tTF | n |
|---|---|---|---|---|---|
| | Day 0 | Day 7 | | | |
| Buffer | 39 ± 3 | 467 ± 137 | | ns | 9 |
| tTF | 44 ± 8 | 764 ± 148 | ns | | 5 |
| tTF-RGD | 45 ± 5 | 130 ± 19 | <0.01 | <0.01 | 10 | ns: not significant

Other tTF fusion proteins can be constructed without any problem by a person skilled in the art on the basis of the disclosure of the present invention. Potential candidates are the peptides TAASGVRSMH (SEQ ID NO:39) and LTLR-WVGLMS (SEQ ID NO:40), which bind to NG 2, the murine homolog of the human melanoma proteoglycan (12). Expression of NG 2 is restricted to tumor cells and angiogenic vessels of a tumor (35). Another candidate is the synthetic peptide TTHWGFTL (SEQ ID NO:41), which produces selective and potent inhibition of matrix metalloproteinase-2 (MMP-2) (13). As the integrin $\alpha_v\beta_3$ evidently also binds MMP-2 in an RGD-independent manner, this means that the active enzyme is localized on the surface of the angiogenic blood vessels (36). A construct consisting of tTF and this MMP-2 inhibitory peptide might similarly mediate the selective binding of $tTF_{1-218}$ to the endothelial cell membrane of tumor vessels.

REFERENCES

1. Folkman J, Watson K, Ingber D, Hanahan D: Induction of angiogenesis during the transition from hyperplasia to neoplasia. Nature 339: 58-61, 1989
2. Dvrorak H J, Sioussat T M, Brown L F, Berse B, Nagy J A, Sotrel A, Manseau E J: Distribution of vascular permeability factor (vascular endothelial growth factor) in tumors-Concentration in tumor blood vessels. J Exp Med 174: 1275-1278, 1991
3. Dvorak H J, Brown L F, Detmar M, Dvorak A M: Vascular permeability factor/vascular endothelial growth factor, microvascular hyperpermeability, and angiogenesis. Am J Pathol 146: 1029-1039, 1995
4. Terman B J, Dougher-Vermazen M: Biological properties of VEGF/VPF receptors. Cancer Metastasis Rev 15: 159-163, 1996
5. Burrows F J, Derbyshire E J, Tazzari P L, Amlot P, Gazdzar A F, King S W, Letarte M, Vitetta E S, Thorpe P E: Upregulation of endoglin on vascular endothelial cells in human solid tumors: Implications for diagnosis and therapy. Clin Cancer Res 1: 1623-1634, 1995
6. Rettig W J, Garinchesa P, Healey J H, Su S L, Jaffe E A, Old L J: Identification of endosialin, a cell surface glycoprotein of vascular endothelial cells in human cancer. Proc Natl Acad Sci USA 89: 10832-10836, 1992
7. Carnemolla B, Balza E, Siri A, Zardi L, Nicrotra M R, Bigotti A, Natali P G: A tumor-associated fibronectin isoform generated by alternative splicing of messenger RNA precursors. J Cell Biol 108: 1139-1148, 1989
8. Arap W, Pasqualini R, Ruoslahti E: Cancer treatment by targeted drug delivery to tumor vasculature in a mouse model. Science 279: 377-380, 1998
9. Senger D R, Claffey K P, Benes J E, Peruzzi C A, Serglou A P, Detmar M: Angiogenesis promoted by vascular endothelial growth factor regulation through $\alpha_1\beta_1$ and $\alpha_2\beta_1$ integrins. Proc Natl Acad Sci USA 94: 13612-13617, 1997
10. Olson T A, Mohanraj D, Roy S, Ramakrishnan S: Targeting the tumor vasculature: inhibition of tumor growth by a vascular endothelial growth factor-toxin conjugate. Int J Cancer 73: 865-870, 1997
11. Bhagwat S V, Lahdenranta J, Giordano R, Arap W, Pasqualini R, Shapiro L H: CD13/APN is activated by angiogenic signals and is essential for capillary tube formation. Blood 97: 652-659, 2001
12. Burg M A, Pasqualini R, Arap W, Ruoslahti E, Stallcup W B: NG2 Proteoglycan-binding peptides target tumor neovasculature. Cancer Res 59: 2869-2874, 1999
13. Koivunen E, Arap W, Valtanen H, Rainisalo A, Medina O P, Heikkila P, Kantor C, Gahmberg C G, Salo T, Konttinen Y T, Sorsa T, Ruoslahti E, Pasqualini R: Tumor targeting with a selective gelatinase inhibitor. Nat Biotechnol 17: 768-774, 1999
14. Huang X, Molema G, King S, Watkins L, Edgington T S, Thorpe P E: Tumor infarction in mice by antibody-directed targeting of tissue factor to tumor vasculature. Science 275: 547-550, 15. Ran S, Gao B, Duffy S, Watkins L, Rote N, Thorpe P E: Infarction of solid Hodgkin's tumors in mice by antibody-directed targeting of tissue factor to tumor vasculature. Cancer Res 58: 4646-4653, 1998
16. Nilsson F, Kosmehl H, Zardi L, Neri D: Targeted delivery of tissue factor to the ED-B domain of fibronectin, a marker of angiogenesis, mediates the infarction of solid tumors in mice. Cancer Res 61: 711-716, 2001
17. Liu C, Huang H, Donate F, Dickinson C, Santucci R, El-Sheikh A, Vessella R, Edgington T S. Prostate-specific membrane antigen directed selective thrombotic infarction of tumors. Cancer Res 62: 5470-5475, 2002
18. Gottstein C, Wels W, Ober B, Thorpe P E: Generation and characterisation of recombinant vascular targeting agents from hybridoma cell lines. BioTechniques 30: 190-200, 2001
19. Morrissey J H, Macik B G, Neuenschwander P F, Comp P C: Quantitation of activated factor VII levels in plasma using a tissue factor mutant selectively deficient in promoting factor VII activation. Blood 81: 734-744, 1993
20. Banner D W, D'Arcy A, Chéne C, Winkler F K, Guha A, Konigsberg W H, Nemerson Y, Kirchhofer D; The crystal structure of the complex of blood coagulation factor VIIa with soluble tissue factor. Nature 380: 41-46, 1996
21. Koivunen E, Gay D A, Ruoslahti E: Selection of peptides binding to the $\alpha_5\beta_1$ integrin from phage display library. J Biol Chem 268: 20205-20210, 1993
22. Healy J M, Murayama O, Maeda T, Yoshino K, Sekiguchi K, Kikuchi M: Peptide ligands for integrin $\alpha_v\beta_3$ selected from random phage display libraries. Biochemistry 34: 3948-3955,
23. Pasqualini R, Koivunen E, Kain R, Lahdenranta J, Sakamoto M, Stryhn A, Ashmun R A, Shapiro L H, Arap W, Ruoslahti E: Aminopeptidase N is a receptor for tumor-homing peptides and a target for inhibiting angiogenesis. Cancer Res 60: 722-727, 2000
24. Curnis F, Sacchi A, Borgna L, Magni F, Gasparri A, Corti A: Enhancement of tumor necrosis factor α antitumor immunotherapeutic properties by targeted delivery to aminopeptidase N (CD 13). Nature Biotechnology 18: 1185-1190, 2000
25. Ellerby H M, Arap W, Ellerby L M, Kain R, Andrusiak R, Del Rio G, Krajewski S, Lombardo C R, Rao R, Ruoslahti E Bredesen D E, Pasqualini R: Anti-cancer activity of targeted proapoptotic peptides. Nature Med 5: 1032-1038, 1999
26. Ruoslahti E: Targeting tumor vasculature with homing peptides from phage display. Cancer Biol 10: 435-442, 2000
27. Pasqualini R, Koivunen E, Kain R, Lahdenranta J, Sakamoto M, Stryhn A, Ashmun R A, Shapiro L H, Arap W, Ruohslahti E. Aminopeptidase N is a receptor for tumor-homing peptides and a target for inhibiting angiogenesis. Cancer Res 60: 722-727, 2000
28. Curnis F, Arrigoni G, Sacchi A, Fischetti L, Arap W, Pasqualini R, Corti A. Differential binding of drugs containing the NGR motif to CD13 isoforms in tumor vessels, epithelia, and myeloid cells. Cancer Res 62: 867-874, 2002
29. Senger D R, Claffey K P, Benes J E, Perruzzi C A, Sergiou A P, Detmar M: Angiogenesis promoted by vascular endothelial growth factor regulation through $\square_1\square_1$ and $\square_2\square_1$ integrins. Proc Natl Acad Sci USA 94: 13612-13617, 1997
30. Yun Z, Menter D G, Nicolson G L: Involvement of integrin $\alpha_1\beta_3$ in cell adhesion, motility and liver metastasis of murine RAW117 large cell lymphoma. Cancer Res 56: 3103-3111, 1996
31. Brooks P C, Clark R A F, Cheresh D A: Requirement of vascular integrin $\alpha_v\beta_3$ for angiogenesis. Science 264; 569-571, 1994
32. Brooks P C, Montgomery A M, Rosenfeld M, Reisfeld R A, Hu T, Klier G, Cheresh D A: Integrin $\alpha_v\beta_3$ antagonists promote tumor regression by inducing apoptosis of angiogenic blood vessels. Cell 92: 391-400, 1998
33. Topp M S, Koenigsmann M, Mire-Sluis A, Oberberg D, Eitelbach F, von Marschall Z, Notter M, Reufi B, Stein H, Thiel E, Berdel W E: Recombinant human interleukin-4 inhibits growth of some human lung tumor cell lines in vitro and in vivo. Blood 82: 2837-2844, 1993
34. Topp M S, Papadimitriou C A, Eltelbach F, Koenigsmann M, Oelmann E, Koehler B, Oberberg D, Reufi B, Stein H, Thiel E, Berdel W E: Recombinant human interleukin 4 has antiproliferative activity on human tumor cell lines derived from epithelial and non-epithelial histologies. Cancer Res 55: 2173-2176, 1995
35. Schrappe M, Klier F G, Spiro R C, Gladson C L: Correlation of chondroitin sulfate proteoglycan expression on proliferating brain capillary endothelial cells with the malignant phenotype of astroglial cells. Cancer Res 51: 4986-4993, 1991
36. Brooks P C: Localization of matrix metalloproteinase MMP-2 to the surface of invasive cells by interaction with integrin $\alpha_v\beta_3$. Cell 85: 683-693, 1996
37. Brooks P C, Silletti S, von Schalscha T L, Friedlander M, Cheresh D A: Disruption of Anglo-genesis by PEX, a non-catalytic metalloproteinase fragment with integrin binding activity. Cell 92: 391-400, 1998
38. Schnurch H, Risau W: Expression of tie2, a member of a novel family of receptor tyrosine kinase in the endothelial cell lineage. Development 119: 957-968, 1993
39. Peters K G, Coogan A, Berry D, Marks J, Iglehart J D, Kontos C D, Rao P, Sankar S, Trogan E: Expression of tie2/tek in breast tumor vasculature provides a new marker for evaluation of tumor angiogenesis. Br J Cancer 77: 51-56, 1998
40. Suri C, Jones P F, Patan S, Bartunkova S, Maisonpierre P C, Davis S, Sato T N, Yancopoulos G D: requisite role of angiopoietin-1, a ligand for the tie2 receptor, during embryonic angiogenesis. Cell 87: 1171-1180, 1996
41. Maisonpierre P C, Suri C, Jones P F, Bartunkova S, Wiegand S J, Radziejewski C, Compton D, McClain J, Aldrich T H, Papadopoulos N, Daly T H, Davis S, Sato T N, Yancopoulos G D: Angiopoietin-2, a natural antagonist for tie2 that disrupts in vivo angiogenesis. Science 277: 55-60, 1997
42. Scholz C C, Berger D P, Winterhalter B R, Henβ H, Fiebig H H: Correlation of drug response in patients and in the clonogenic assay with solid human tumour xenografts. Eur J Cancer 26: 901-905, 1990
43. Fiebig H H, Berger D P, Dengler W A, Wallbrecher E, Winterhalter B R: Combined in vitro/in vivo test procedure with human tumor xenografts for new drug development. Contrib. Oncol. Basel, Karger 42: 321-351, 1992.
44. Fiebig H H. Burger A M: Human tumor xenografts and explants. Tumor Models in Cancer Research, eds B. A. Teicher, Humana Press Inc., Totowa, N.J., 2002.
45. Ruf W, Rehemtulla A, Edgington T S: Phospholipid-independent and -dependent Interactions required for tissue factor receptor and cofactor function. J Biol Chem 266: 2158-2166, 1991.
46. Hu P, Yan J, Sharifi J, Bai T, Khawla L A, Epstein A L: Comparison of three different targeted tissue factor fusion proteins for inducing tumor vessel thrombosis. Cancer Research 63: 5046-5053.

The invention claimed is:

1. A fusion polypeptide comprising an amino acid sequence selected from the group consisting of SEQ ID NOS: 3, 4, 6, 7, and 8.

2. A fusion polypeptide consisting of an amino acid sequence selected from the group consisting of SEQ ID NOS: 3, 4, 6, 7, and 8.

3. A nucleic acid comprising a nucleotide sequence encoding the fusion polypeptide of claim 1 or 2.

4. A vector comprising the nucleic acid of claim 3.

5. An isolated host cell comprising the vector of claim 4.

6. A composition comprising the vector of claim 5 and a pharmaceutically acceptable carrier, excipient, or adjuvant.

7. A composition comprising the host cell of claim 4 and a pharmaceutically acceptable carrier, excipient, or adjuvant.

8. An isolated host cell comprising the nucleic acid of claim 3.

9. A composition comprising the nucleic acid of claim 3 and a pharmaceutically acceptable carrier, excipient, or adjuvant.

10. A nucleic acid consisting of a nucleotide sequence encoding the fusion polypeptide of claim 1 or 2.

11. A composition comprising the fusion polypeptide of claim 1 or 2 and a pharmaceutically acceptable carrier, excipient, or adjuvant.

12. A nucleic acid comprising a nucleotide sequence selected from the group consisting of SEQ ID NOS: 10, 11, 13, 14, and 15.

13. A nucleic acid consisting of a nucleotide sequence selected from the group consisting of SEQ ID NOS: 10, 11, 13, 14, and 15.

14. A vector comprising the nucleic acid of claim 12 or 13.

15. An isolated host cell comprising the vector of claim 14.

16. A composition comprising the nucleic acid of claim 12 and a pharmaceutically acceptable carrier, excipient, or adjuvant.

17. A method of treating a patient with a neoplastic disease comprising administering to said patient a fusion polypeptide of SEQ ID NO: 3 or 4 in an amount effective to inhibit tumor growth.

18. The method according to claim 17, wherein said administering is selected from the group consisting of intravenous, subcutaneous, oral, and intraperitoneal administration, wherein said oral administration is of a gastrointestinal cleavage resistant formulation.

19. A method of treating a patient with a neoplastic disease comprising administering to said patient a fusion polypeptide of SEQ ID NO: 3 or 4 in an amount effective to reduce the size of the tumors in the patient.

20. The method according to claim 19, wherein said administering is selected from the group consisting of intravenous, subcutaneous, oral, and intraperitoneal administration, wherein said oral administration is of a gastrointestinal cleavage resistant formulation.

21. A method of treating a patient with a neoplastic disease comprising administering to said patient a composition comprising the fusion polypeptide of SEQ ID NO: 3 or 4 and a pharmaceutically acceptable carrier, excipient, or adjuvant in an amount effective to inhibit tumor growth.

22. The method according to claim 21, wherein said administering is selected from the group consisting of intravenous, subcutaneous, oral, and intraperitoneal administration, wherein said oral administration is of a gastrointestinal cleavage resistant formulation.

23. A method of treating a patient with a neoplastic disease comprising administering to said patient a composition comprising the fusion polypeptide of SEQ ID NO: 3 or 4 and a pharmaceutically acceptable carrier, excipient, or adjuvant in an amount effective to reduce the size of the tumors in the patient.

24. The method according to claim 23, wherein said administering is selected from the group consisting of intravenous, subcutaneous, oral, and intraperitoneal administration, wherein said oral administration is of a gastrointestinal cleavage resistant formulation.

* * * * *